United States Patent
Cheng et al.

(10) Patent No.: US 11,225,482 B2
(45) Date of Patent: Jan. 18, 2022

(54) DIHYDROPYRROLOPYRIMIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Xingchun Han, Shanghai (CN); Min Jiang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 180 days.

(21) Appl. No.: 16/227,136

(22) Filed: Dec. 20, 2018

(65) Prior Publication Data

US 2019/0241570 A1    Aug. 8, 2019

Related U.S. Application Data

(63) Continuation of application No. PCT/EP2017/065672, filed on Jun. 26, 2017.

(51) Int. Cl.
| | |
|---|---|
| *C07D 487/04* | (2006.01) |
| *A61K 31/4985* | (2006.01) |
| *A61K 31/4353* | (2006.01) |
| *A61P 31/20* | (2006.01) |
| *C07D 519/00* | (2006.01) |
| *C07D 491/107* | (2006.01) |

(52) U.S. Cl.
CPC ........... *C07D 487/04* (2013.01); *A61P 31/20* (2018.01); *C07D 491/107* (2013.01); *C07D 519/00* (2013.01)

(58) Field of Classification Search
CPC .................................................. C07D 487/04
See application file for complete search history.

(56) References Cited

U.S. PATENT DOCUMENTS

2002/0161029 A1    10/2002    Paget et al.

FOREIGN PATENT DOCUMENTS

| | | |
|---|---|---|
| DE | 10 2007 041 116 A1 | 3/2009 |
| JP | 2004-518724 A | 6/2004 |
| JP | 2005-520815 A | 7/2005 |
| JP | 2014-510122 A | 4/2014 |
| WO | 01/42242 A1 | 6/2001 |
| WO | 02/064574 A2 | 8/2002 |
| WO | 2006/082001 A1 | 8/2006 |
| WO | 2009/030316 A1 | 3/2009 |
| WO | 2012/136622 A1 | 10/2012 |
| WO | 2013/049352 A2 | 4/2013 |
| WO | 2016/107832 A1 | 7/2016 |
| WO | 2016/177655 A1 | 11/2016 |

OTHER PUBLICATIONS

Geng et al., "Small-molecule inhibitors for the treatment of hepatitis B virus documented in patents" Mini Reviews in Medicinal Chemistry 13(5):749-776 (2013).
International Preliminary Report on Patentability for PCT/EP2017/065672 dated Jan. 1, 2019.
International Search Report and Written Opinion for PCT/EP2017/065672 dated Jul. 31, 2017.

*Primary Examiner* — Emily A Bernhardt
*Assistant Examiner* — Laura M Daniel
(74) *Attorney, Agent, or Firm* — Genentech, Inc.; Richard G. A. Bone

(57) ABSTRACT

The present invention provides novel compounds having the general formula:

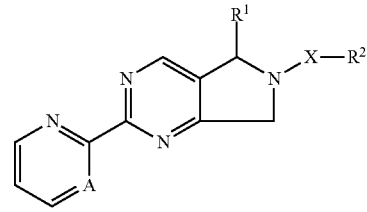

wherein $R^1$, $R^2$, A and X are as described herein, compositions including the compounds and methods of using the compounds.

17 Claims, No Drawings

DIHYDROPYRROLOPYRIMIDINES FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel dihydropyrrolopyrimidines having pharmaceutical activity, their manufacture, pharmaceutical compositions containing them and their potential use as medicaments.

The present invention relates to compounds of formula I

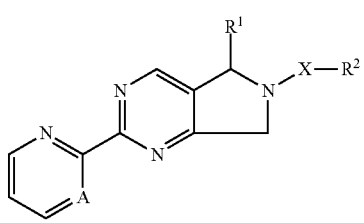

(I)

wherein $R^1$, $R^2$, A and X are as described below, or a pharmaceutically acceptable salt, or enantiomer, or diastereomer thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Nayersina et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. PLoS One, (2011), 6, e15324; Shi et al. *J Viral Hepat.* (2012), 19, e26-33; Kondo et al. *ISRN Gasteroenterology,* (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet,* (2005), 365, 123-9; Marcellin et al. *N. Engl. J. Med.,* (2004), 351, 1206-17; Buster et al. *Hepatology,* (2007), 46, 388-94). Therefore, there is an unmet medical need to target HBsAg for HBV treatment (Wieland, S. F. & F. V. Chisari. *J Virol,* (2005), 79, 9369-80; Kumar et al. *J Virol,* (2011), 85, 987-95; Woltman et al. *PLoS One,* (2011), 6, e15324; Op den Brouw et al. *Immunology,* (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I,

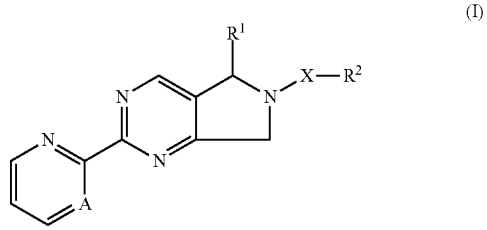

(I)

wherein
R$^1$ is aminoC$_{1-6}$alkyl, C$_{1-6}$alkyl, C$_{3-7}$cycloalkyl, carboxyC$_{1-6}$alkyl, cyanoC$_{1-6}$alkyl, haloC$_{1-6}$alkyl, hydrogen or hydroxyC$_{1-6}$alkyl;
R$^2$ is phenyl, naphthyl, or heteroaryl, wherein said phenyl, naphthyl and heteroaryl is unsubstituted or substituted with one, two or three substituents independently selected from 2-oxa-6-azaspiro[3.3]heptanyl, azetidinyl, C$_{1-6}$alkoxy, C$_{1-6}$alkyl, C$_{1-6}$alkylamino, C$_{1-6}$alkylcarbonylpiperazinyl, C$_{1-6}$alkylsulfonylpiperazinyl, diC$_{1-6}$alkylamino, haloC$_{1-6}$alkyl, halogen, morpholinyl, nitro, oxopiperazinyl, piperazinyl, piperidinyl and pyrrolidinyl;
A is N or CH;
X is a bond or —C(=O)—;
or a pharmaceutically acceptable salt, or enantiomer, or diastereomer thereof.

DETAILED DESCRIPTION OF THE INVENTION

Definitions

As used herein, the term "C$_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "C$_{1-6}$alkyl" groups are methyl, ethyl, isopropyl and tert-butyl. More particularly "C$_{1-6}$alkyl" group is methyl.

The term "C$_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" groups are cyclopropyl, cyclobutyl, cyclopentyl and cyclohexyl.

The term "C$_{1-6}$alkoxy" alone or in combination signifies a group C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy. More particularly "C$_{1-6}$alkoxy" group is methoxy.

The term "halogen" means fluorine, chlorine, bromine or iodine.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is trifluoromethyl.

The term "amino" denotes a group of the formula —NR'R" wherein R' and R" are independently hydrogen or C$_{1-6}$alkyl. Alternatively, R' and R", together with the nitrogen to which they are attached, can form a heteroC$_{3-7}$cycloalkyl.

The term "carbonyl" alone or in combination refers to the group —C(O)—.

The term "cyano" alone or in combination refers to the group —CN.

The term "C$_{1-6}$alkylsulfonyl" denotes a group —SO$_2$-C$_{1-6}$alkyl, wherein C$_{1-6}$alkyl group is defined above. Examples of C$_{1-6}$alkylsulfonyl include methylsulfonyl and ethylsulfonyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, indazolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, imidazo[1,2-a]pyridinyl, pyrazolo[1,5-a]pyridinyl or quinoxalinyl. Particular "heteroaryl" groups are 1,2-benzoxazolyl, 1,3-benzothiazolyl, benzimidazolyl, benzofuranyl, imidazo[1,2-a]pyridinyl, indazolyl, pyrazinyl, pyrazolo[1,5-a]pyridinyl, pyrazolyl, pyridinyl, thiazolyl and thienyl.

The term "halothienyl" denotes a thienyl substituted once, twice or three times by halogen. Examples of halothienyl include, but not limited to, bromothienyl, chlorothienyl, fluorothienyl, difluorothienyl and fluorochlorothienyl. Particular "halothienyl" groups are bromothienyl and chlorothienyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

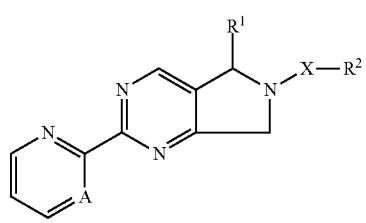

wherein
$R^1$ is amino$C_{1-6}$alkyl, $C_{3-7}$cycloalkyl, carboxy$C_{1-6}$alkyl, cyano$C_{1-6}$alkyl, halo$C_{1-6}$alkyl, hydrogen or hydroxy$C_{1-6}$alkyl;
$R^2$ is phenyl, naphthyl, or heteroaryl, wherein said phenyl, naphthyl and heteroaryl are unsubstituted or substituted with one, two or three substituents independently selected from 2-oxa-6-azaspiro[3.3]heptanyl, azetidinyl, $C_{1-6}$alkoxy, $C_{1-6}$alkyl, $C_{1-6}$alkylamino, $C_{1-6}$alkylcarbonylpiperazinyl, $C_{1-6}$alkylsulfonylpiperazinyl, di$C_{1-6}$alkylamino, halo$C_{1-6}$alkyl, halogen, morpholinyl, nitro, oxopiperazinyl, piperazinyl, piperidinyl and pyrrolidinyl;
A is N or CH;
X is a bond or —C(=O)—;
or a pharmaceutically acceptable salt, or enantiomer, or diastereomer thereof.

A further embodiment of the present invention is (ii) a compound of formula I, wherein
$R^1$ is $C_{1-6}$alkyl or hydrogen;
$R^2$ is phenyl, naphthyl or heteroaryl, wherein said phenyl and heteroaryl are unsubstituted or substituted with one, two or three substituents independently selected from 2-oxa-6-azaspiro[3.3]heptanyl, azetidinyl, $C_{1-6}$alkoxy, $C_{1-6}$alkyl, $C_{1-6}$alkylamino, $C_{1-6}$alkylcarbonylpiperazinyl, $C_{1-6}$alkylsulfonylpiperazinyl, di$C_{1-6}$alkylamino, halo$C_{1-6}$alkyl, halogen, morpholinyl, nitro, oxopiperazinyl, piperazinyl, piperidinyl and pyrrolidinyl;
A is N or CH;
X is a bond or —C(=O)—;
or a pharmaceutically acceptable salt, or enantiomer, or diastereomer thereof.

Another embodiment of the present invention is (iii) a compound of formula I, wherein
$R^1$ is $C_{1-6}$alkyl;
$R^2$ is phenyl, naphthyl or heteroaryl, wherein said phenyl and heteroaryl are unsubstituted or substituted with one, two or three substituents independently selected from $C_{1-6}$alkyl, $C_{1-6}$alkoxy, halo$C_{1-6}$alkyl, halogen and nitro; said heteroaryl is 1,2-benzoxazolyl, 1,3-benzothiazolyl, benzimidazolyl, indazolyl, benzofuranyl, imidazo[1,2-a]pyridinyl, pyrazinyl, pyrazolo[1,5-a]pyridinyl, pyrazolyl, thiazolyl or thienyl;
A is N;
X is —C(=O)—;
or a pharmaceutically acceptable salt, or enantiomer, or diastereomer thereof.

Another embodiment of the present invention is (iv) a compound of formula I, or a pharmaceutically acceptable salt, or enantiomer, or diastereomer thereof, wherein $R^1$ is methyl, and all remaining substituents have the significances given herein before.

Another embodiment of the present invention is (v) a compound of formula I, or a pharmaceutically acceptable salt, or enantiomer, or diastereomer thereof, wherein $R^2$ is indazolyl, $C_{1-6}$alkylindazolyl, $C_{1-6}$alkoxythienyl, $C_{1-6}$alkylthienyl or halothienyl, and all remaining substituents have the significances given herein before.

A further embodiment of the present invention is (vi) a compound of formula I, or a pharmaceutically acceptable salt, or enantiomer, or diastereomer thereof, wherein $R^2$ is indazolyl, methylindazolyl, methoxythienyl, bromothienyl or chlorothienyl, and all remaining substituents have the significances given herein before.

Another embodiment of the present invention is (vii) a compound selected from
(5-methyl-2-pyrimidin-2-yl-5,7-dihydropyrrolo[3,4-d]pyrimidin-6-yl)-(5-methylthiazol-2-yl)methanone;
(5-methoxy-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-[4-(trifluoromethyl)thiazol-2-yl]methanone;
(3-fluoro-5-methoxy-phenyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(2-thienyl)methanone;
(5-methyl-2-pyrimidin-2-yl-5,7-dihydropyrrolo[3,4-d]pyrimidin-6-yl)-(4-methyl-2-thienyl)methanone;

(4-bromo-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(5-methyl-2-thienyl)methanone;
(5-chloro-2-thienyl)-(5-methyl-2-pyrimidin-2-yl-5,7-dihydropyrrolo[3,4-d]pyrimidin-6-yl)methanone;
(4,5-dimethylthiazol-2-yl)-(5-methyl-2-pyrimidin-2-yl-5,7-dihydropyrrolo[3,4-d]pyrimidin-6-yl)methanone;
(1-methylpyrazol-4-yl)-(5-methyl-2-pyrimidin-2-yl-5,7-dihydropyrrolo[3,4-d]pyrimidin-6-yl)methanone;
(1-methylindazol-3-yl)-(5-methyl-2-pyrimidin-2-yl-5,7-dihydropyrrolo[3,4-d]pyrimidin-6-yl)methanone;
(1-methylpyrazol-3-yl)-(5-methyl-2-pyrimidin-2-yl-5,7-dihydropyrrolo[3,4-d]pyrimidin-6-yl)methanone;
1H-benzimidazol-2-yl-(5-methyl-2-pyrimidin-2-yl-5,7-dihydropyrrolo[3,4-d]pyrimidin-6-yl)methanone;
(4-methoxyphenyl)-(5-methyl-2-pyrimidin-2-yl-5,7-dihydropyrrolo[3,4-d]pyrimidin-6-yl)methanone;
(1-ethylpyrazol-3-yl)-(5-methyl-2-pyrimidin-2-yl-5,7-dihydropyrrolo[3,4-d]pyrimidin-6-yl)methanone;
(5-bromo-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(5-nitro-2-thienyl)methanone;
(5-methyl-2-pyrimidin-2-yl-5,7-dihydropyrrolo[3,4-d]pyrimidin-6-yl)-(2-naphthyl)methanone;
imidazo[1,2-a]pyridin-2-yl-(5-methyl-2-pyrimidin-2-yl-5,7-dihydropyrrolo[3,4-d]pyrimidin-6-yl)methanone;
(3-methylbenzofuran-2-yl)-(5-methyl-2-pyrimidin-2-yl-5,7-dihydropyrrolo[3,4-d]pyrimidin-6-yl)methanone;
(6-methoxypyrazin-2-yl)-(5-methyl-2-pyrimidin-2-yl-5,7-dihydropyrrolo[3,4-d]pyrimidin-6-yl)methanone;
1H-indazol-3-yl-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-pyrazolo[1,5-a]pyridin-3-yl-methanone;
1,3-benzothiazol-6-yl-(5-methyl-2-pyrimidin-2-yl-5,7-dihydropyrrolo[3,4-d]pyrimidin-6-yl)methanone;
imidazo[1,2-a]pyridin-3-yl-(5-methyl-2-pyrimidin-2-yl-5,7-dihydropyrrolo[3,4-d]pyrimidin-6-yl)methanone;
1,2-benzoxazol-3-yl-(5-methyl-2-pyrimidin-2-yl-5,7-dihydropyrrolo[3,4-d]pyrimidin-6-yl)methanone; and
1,3-benzothiazol-2-yl-(5-methyl-2-pyrimidin-2-yl-5,7-dihydropyrrolo[3,4-d]pyrimidin-6-yl)methanone;
or a pharmaceutically acceptable salt, or enantiomer, or diastereomer thereof.

A further embodiment of the present invention is (viii) a compound which is (1-methylindazol-3-yl)-(5-methyl-2-pyrimidin-2-yl-5,7-dihydropyrrolo[3,4-d]pyrimidin-6-yl)methanone; or a pharmaceutically acceptable salt, or enantiomer, or diastereomer thereof.

Another embodiment of the present invention is (ix) a compound of formula I, wherein
$R^1$ is $C_{1-6}$alkyl or hydrogen;
$R^2$ is phenyl substituted with one, two or three substituents independently selected from halogen and $C_{1-6}$alkoxy; or pyridinyl substituted with one or two substituents independently selected from $C_{1-6}$alkoxy, 2-oxa-6-azaspiro[3.3]heptanyl, azetidinyl, $C_{1-6}$alkylamino, $C_{1-6}$alkylcarbonylpiperazinyl, $C_{1-6}$alkylsulfonylpiperazinyl, di$C_{1-6}$alkylamino, halogen, morpholinyl, oxopiperazinyl, piperazinyl, piperidinyl and pyrrolidinyl;
A is N or C;
X is a bond;
or a pharmaceutically acceptable salt, or enantiomer, or diastereomer thereof.

Another embodiment of the present invention is (x) a compound of formula I, or a pharmaceutically acceptable salt, or enantiomer, or diastereomer thereof, wherein $R^1$ is methyl, and all remaining substituents have the significances given herein before.

Another embodiment of the present invention is (xi) a compound of formula I, or a pharmaceutically acceptable salt, or enantiomer, or diastereomer thereof, wherein $R^2$ is pyridinyl substituted with one or two substituents independently selected from $C_{1-6}$alkoxy, azetidinyl, $C_{1-6}$alkylamino, $C_{1-6}$alkylsulfonylpiperazinyl, di$C_{1-6}$alkylamino, halogen, and oxopiperazinyl, and all remaining substituents have the significances given herein before.

A further embodiment of the present invention is (xii) a compound of formula I, or a pharmaceutically acceptable salt, or enantiomer, or diastereomer thereof, wherein $R^2$ is pyridinyl substituted with one or two substituents independently selected from methoxy, azetidinyl, methylamino, methylsulfonylpiperazinyl, dimethylamino, fluoro and oxopiperazinyl, and all remaining substituents have the significances given herein before.

Another embodiment of the present invention is (xiii) a compound of formula I, or a pharmaceutically acceptable salt, or enantiomer, or diastereomer thereof, wherein A is N, and all remaining substituents have the significances given herein before.

Another embodiment of the present invention is (xiv) a compound selected from
6-(3,4-difluoro-5-methoxy-phenyl)-2-(2-pyridyl)-5,7-dihydropyrrolo[3,4-d]pyrimidine;
6-(6-fluoro-4-methoxy-2-pyridyl)-5-methyl-2-pyrimidin-2-yl-5,7-dihydropyrrolo[3,4-d]pyrimidine;
6-(4,6-difluoro-2-pyridyl)-5-methyl-2-pyrimidin-2-yl-5,7-dihydropyrrolo[3,4-d]pyrimidine;
6-(2,6-difluoro-4-pyridyl)-5-methyl-2-pyrimidin-2-yl-5,7-dihydropyrrolo[3,4-d]pyrimidine;
6-(6-fluoro-4-methoxy-2-pyridyl)-5-methyl-2-(2-pyridyl)-5,7-dihydropyrrolo[3,4-d]pyrimidine;
1-[4-[4-fluoro-6-(5-methyl-2-pyrimidin-2-yl-5,7-dihydropyrrolo[3,4-d]pyrimidin-6-yl)-2-pyridyl]piperazin-1-yl]ethanone;
6-[6-fluoro-4-(5-methyl-2-pyrimidin-2-yl-5,7-dihydropyrrolo[3,4-d]pyrimidin-6-yl)-2-pyridyl]-2-oxa-6-azaspiro[3.3]heptane;
6-[2-fluoro-6-(5-methyl-2-pyrimidin-2-yl-5,7-dihydropyrrolo[3,4-d]pyrimidin-6-yl)-4-pyridyl]-2-oxa-6-azaspiro[3.3]heptane;
2-fluoro-N-methyl-6-(5-methyl-2-pyrimidin-2-yl-5,7-dihydropyrrolo[3,4-d]pyrimidin-6-yl)pyridin-4-amine;
2-fluoro-N,N-dimethyl-6-(5-methyl-2-pyrimidin-2-yl-5,7-dihydropyrrolo[3,4-d]pyrimidin-6-yl)pyridin-4-amine;
6-[4-(azetidin-1-yl)-6-fluoro-2-pyridyl]-5-methyl-2-pyrimidin-2-yl-5,7-dihydropyrrolo[3,4-d]pyrimidine;
6-(6-fluoro-4-pyrrolidin-1-yl-2-pyridyl)-5-methyl-2-pyrimidin-2-yl-5,7-dihydropyrrolo[3,4-d]pyrimidine;
6-[6-fluoro-4-(1-piperidyl)-2-pyridyl]-5-methyl-2-pyrimidin-2-yl-5,7-dihydropyrrolo[3,4-d]pyrimidine;
4-[2-fluoro-6-(5-methyl-2-pyrimidin-2-yl-5,7-dihydropyrrolo[3,4-d]pyrimidin-6-yl)-4-pyridyl]morpholine;
6-(6-fluoro-4-piperazin-1-yl-2-pyridyl)-5-methyl-2-pyrimidin-2-yl-5,7-dihydropyrrolo[3,4-d]pyrimidine;
6-[6-fluoro-4-(4-methylsulfonylpiperazin-1-yl)-2-pyridyl]-5-methyl-2-pyrimidin-2-yl-5,7-dihydropyrrolo[3,4-d]pyrimidine; and 4-[2-fluoro-6-(5-methyl-2-pyrimidin-2-yl-5,7-dihydropyrrolo[3,4-d]pyrimidin-6-yl)-4-pyridyl]piperazin-2-one;
or a pharmaceutically acceptable salt, or enantiomer, or diastereomer thereof.

A further embodiment of the present invention is (xv) a compound selected from 6-(6-fluoro-4-methoxy-2-pyridyl)-5-methyl-2-pyrimidin-2-yl-5,7-dihydropyrrolo[3,4-d]pyrimidine;

2-fluoro-N-methyl-6-(5-methyl-2-pyrimidin-2-yl-5,7-dihydropyrrolo[3,4-d]pyrimidin-6-yl)pyridin-4-amine;

2-fluoro-N,N-dimethyl-6-(5-methyl-2-pyrimidin-2-yl-5,7-dihydropyrrolo[3,4-d]pyrimidin-6-yl)pyridin-4-amine;

6-[4-(azetidin-1-yl)-6-fluoro-2-pyridyl]-5-methyl-2-pyrimidin-2-yl-5,7-dihydropyrrolo[3,4-d]pyrimidine;

6-[6-fluoro-4-(4-methylsulfonylpiperazin-1-yl)-2-pyridyl]-5-methyl-2-pyrimidin-2-yl-5,7-dihydropyrrolo[3,4-d]pyrimidine; and 4-[2-fluoro-6-(5-methyl-2-pyrimidin-2-yl-5,7-dihydropyrrolo[3,4-d]pyrimidin-6-yl)-4-pyridyl]piperazin-2-one;
or a pharmaceutically acceptable salt, or enantiomer, or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$, A and X are as defined above unless otherwise indicated. Furthermore, and unless explicitly otherwise stated, all reactions, reaction conditions, abbreviations and symbols have the meanings well known to a person of ordinary skill in organic chemistry.

General synthetic route for Compound Ia (Scheme 1)

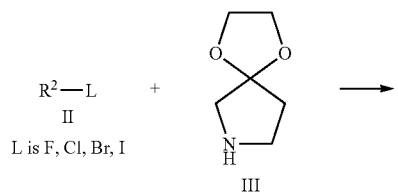

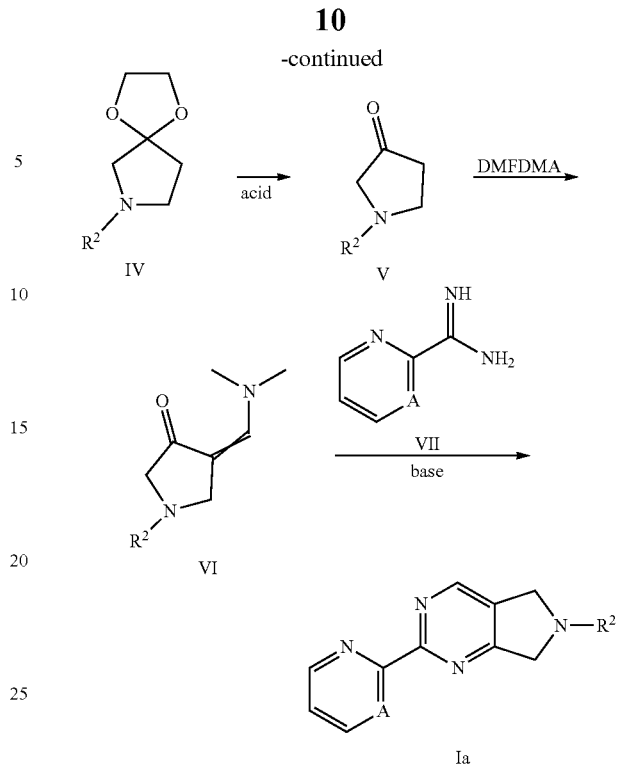

The compound of formula Ia can be prepared according to Scheme 1.

Coupling of compound II with compound III, in the presence or absence of a catalyst such as $Pd_2(dba)_3$ or $Pd(OAc)_2$, a ligand such as Ruphos or BINAP and a base such as $Cs_2CO_3$, $K_2CO_3$, or t-BuONa, in a suitable solvent such as 1,4-dioxane, DMSO or toluene, affords compound IV. Deprotection of compound IV under acidic condition affords compound V. Reaction of compound V with DMFDMA in the absence or presence of a suitable solvent such as DMF or acetonitrile generates intermediate VI. Compound Ia can be obtained by cyclization of intermediate VI with compound VII in the presence of a base such as $K_2CO_3$, NaOMe or $Et_3N$, in a suitable solvent such as EtOH or MeOH.

General synthetic route for Compound Ib-A, Ib-B and Ib-C (Scheme 2)

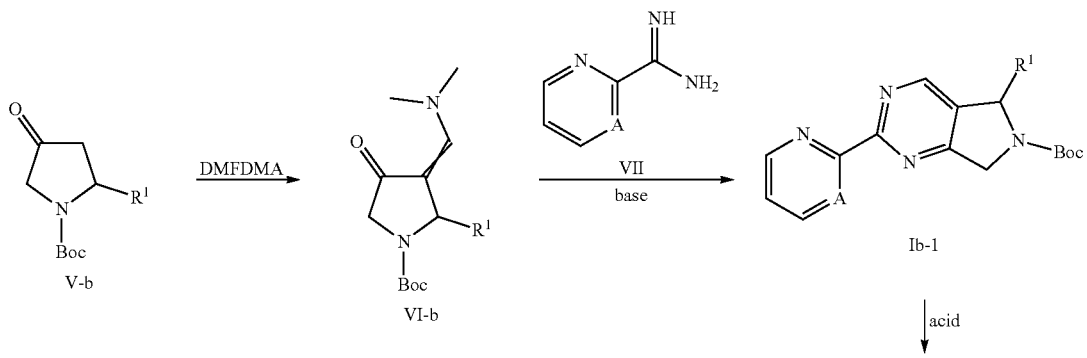

-continued

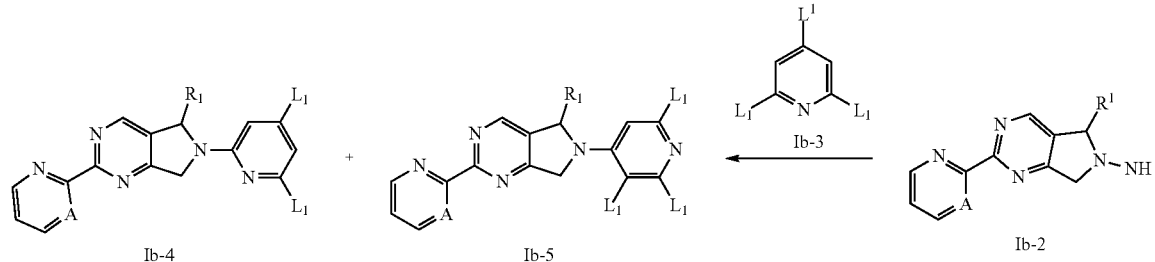

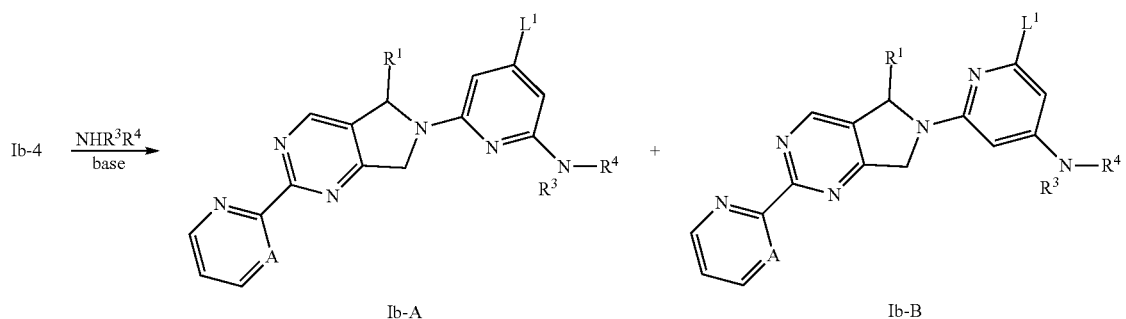

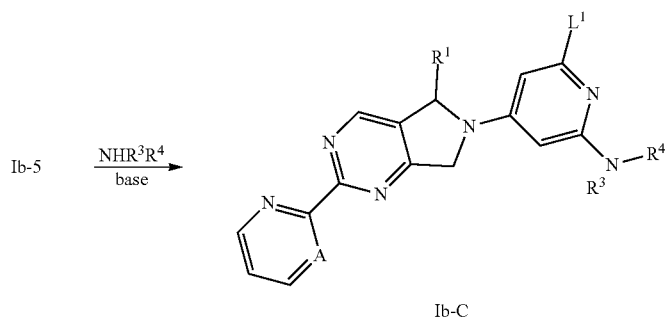

The compound of formula Ib-A, Ib-B and Ib-C can be prepared according to Scheme 2, wherein $L^1$ is F, Cl or Br; $R^3$ and $R^4$ are independently selected from hydrogen or $C_{1-6}$alkyl; or $R^3$ and $R^4$ together with the nitrogen to which they are attached form 2-oxa-6-azaspiro[3.3]heptanyl, azetidinyl, $C_{1-6}$alkylcarbonylpiperazinyl, $C_{1-6}$alkylsulfonylpiperazinyl, morpholinyl, oxopiperazinyl, piperazinyl, piperidinyl and pyrrolidinyl.

Treatment of V-b with DMFDMA in the presence or absence of a suitable solvent such as DMF and $CH_3CN$ produces intermediate VI-b. Cyclization of VI-b with compound VII affords compound Ib-1. The reaction can be carried out in the presence of a suitable base such as NaOMe, NaHCO$_3$ or K$_2$CO$_3$ in a suitable solvent such as MeOH or EtOH. Deprotection of compound Ib-1 with an acid such as HCl or TFA generates intermediate Ib-2. Coupling of compound Ib-2 with halopyridine Ib-3 in the presence of a suitable base such as DIPEA in a suitable solvent such as DMSO or NMP gives compound Ib-4 and Ib-5. Compound Ib-A, Ib-B and Ib-C can be obtained by reaction of compound Ib-4 or Ib-5 with amine NHR$^3$R$^4$ in the presence of a suitable base such as K$_2$CO$_3$ or DIPEA in a suitable solvent such as NMP or DMSO, respectively.

General synthetic route for Compound Ic (Scheme 3)

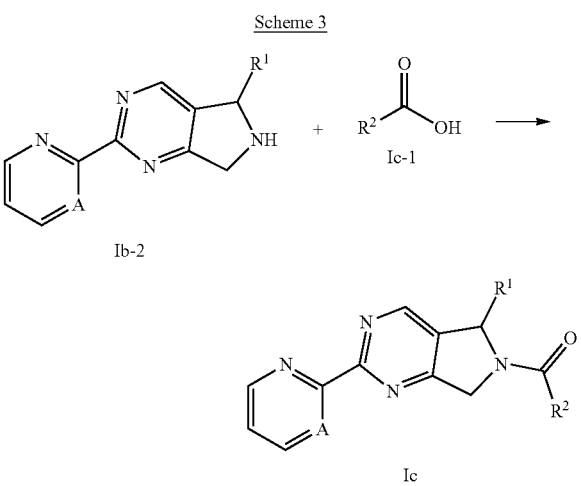

The compound of formula Ic can be prepared according to Scheme 3. Coupling of Ib-2 with Ic-1 in the presence of a condensing agent such as HATU and a base such as DIPEA affords Ic.

This invention also relates to a process for the preparation of a compound of formula I comprising one of the following steps:

(a) cyclization of a compound of formula (A)

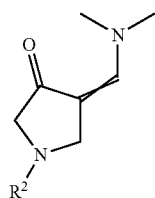
(A)

with a compound of formula (B)

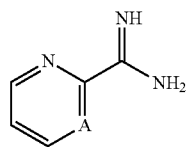
(B)

in the presence of a base;

(b) coupling of a compound of formula (C)

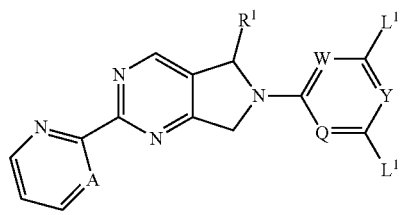
(C)

with a compound of formula (D)

(D)

NHR³R⁴ in the presence of a base; and (c) coupling of a compound of formula (E)

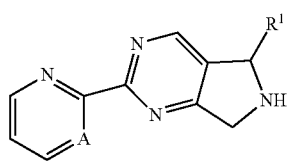
(E)

with a compound of formula (F)

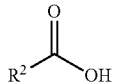
(F)

in the presence of a coupling reagent and a base;
wherein
R¹, R², A and X are defined as above;
L¹ is F, Cl or Br;
One of W, Q and Y is N, the other two are CH;
R³ and R⁴ are independently selected from hydrogen or C₁₋₆alkyl; or
R³ and R⁴ together with the nitrogen to which they are attached form 2-oxa-6-azaspiro[3.3]heptanyl, azetidinyl, C₁₋₆alkylcarbonylpiperazinyl, C₁₋₆alkylsulfonylpiperazinyl, morpholinyl, oxopiperazinyl, piperazinyl, piperidinyl and pyrrolidinyl, In step (a), the base can be for example K₂CO₃, NaOMe or Et₃N;

In step (b), the base can be for example K₂CO₃ or DIEA;

In step (c), the coupling reagent can be for example HATU; the base can be for example DIPEA.

A compound of formula I when manufactured according to the above process is also an object of the invention.

Pharmaceutical Compositions and Administration

The invention also relates to a compound of formula I for use as therapeutically active sub stance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

EXAMPLE A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter (Boc)₂O: di-tert-butyl dicarbonate
BSA: bovine serum albumin
IC$_{50}$: the half maximal inhibitory concentration
LC/MS: liquid chromatography/mass spectrometry
M: molarity
MHz: megahertz
hr(s): hour(s)
mM: millimoles per liter
MS (ESI): mass spectroscopy (electron spray ionization)
nM: nanomoles per liter
NMR: nuclear magnetic resonance
obsd. observed
rt: room temperature
Pd/C: palladium on activated carbon
Pd$_2$(dba)$_3$: Tris(dibenzylideneacetone)dipalladium(0)
TFA: trifluoroacetic acid
δ: chemical shift
Xantphos 4,5-Bis(diphenylphosphino)-9,9-dimethylxanthene
DMFDMA: N,N-dimethylformamide dimethyl acetal
tert-BuONa: sodium tert-butoxide
tert-BuOK: potassium tert-butoxide
DIPEA: N,N-diisopropylethylamine
TEA triethylamine
NMP: N-methyl-2-pyrrolidone
HATU N-[(Dimethylamino)-1H-1,2,3-triazolo-[4,5-b]pyridin-1-ylmethylene]-N-methylmethanaminium hexafluorophosphate N-oxide General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;

Basic condition: A: 0.05% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)⁺.

The microwave assisted reactions were carried out in a Biotage initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

(5-Methyl-2-pyrimidin-2-yl-5,7-dihydropyrrolo[3,4-d]pyrimidin-6-yl)-(5-methylthiazol-2-yl)methanone

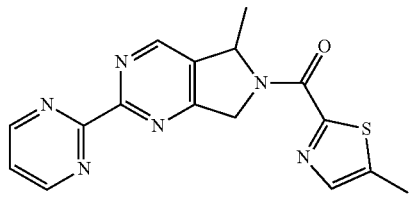 [SMILES: Cc1cnc(C(=O)N2Cc3nc(-c4ncccn4)ncc3C2C)s1]

Step 1: Preparation of methyl 3-(benzylamino)butanoate

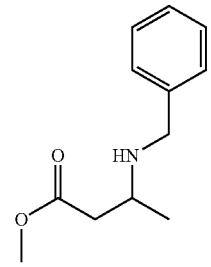

A mixture of methyl crotonate (20.0 g, 200.0 mmol), benzylamine (10.7 g, 100.0 mmol) in MeOH (500 mL) was stirred at rt for 72 hrs. The resulting reaction mixture was concentrated in vacuo to give crude methyl 3-(benzylamino)butanoate (20.3 g) as colorless oil, which was used in the next step without any further purification.

Step 2: Preparation of methyl 3-[benzyl-(2-ethoxy-2-oxo-ethyl)amino]butanoate

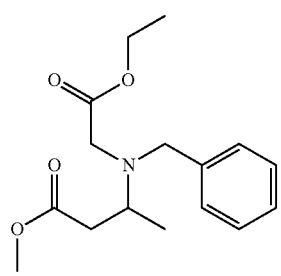 [SMILES: CCOC(=O)CN(Cc1ccccc1)C(C)CC(=O)OC]

A mixture of methyl 3-(benzylamino)butanoate (20.3 g, 97.9 mmol), ethyl bromoacetate (19.3 g, 115.5 mmol) and K$_2$CO$_3$ (27.1 g, 195.8 mmol) in MeCN (275 mL) was stirred at rt for 15 hrs. The resulting reaction mixture was filtered and the filtrate was concentrated in vacuo. The residue was purified by column (eluting with PE/EA=1:1, v:v) to give methyl 3-[benzyl-(2-ethoxy-2-oxo-ethyl)amino]-butanoate (20.5 g) as colorless oil.

Step 3: Preparation of methyl 1-benzyl-2-methyl-4-oxo-pyrrolidine-3-carboxylate

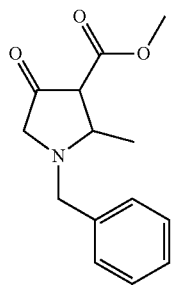 [SMILES: COC(=O)C1C(=O)CN(Cc2ccccc2)C1C]

To a solution methyl 3-[benzyl-(2-ethoxy-2-oxo-ethyl)amino]-butanoate (20.5 g, 69.9 mmol) in toluene (500 mL) was added a solution of tert-BuOK (9.4 g, 83.9 mmol) in THF (150 mL) slowly at 0° C. under N₂ atmosphere. The resulting mixture was stirred at rt for 15 hrs. To the resulting mixture was added HCl (1M, 135 mL, in H₂O). After being stirred at rt for 4 hrs, the resulting mixture was then neutralized with Na₂CO₃. The aqueous layer was separated and extracted with EA (100 mL) for three times. The combined organic layer was dried over anhydrous Na₂SO₄ and concentrated in vacuo. The residue was purified by column (eluting with PE/EA=3/1.v:v) to give methyl 1-benzyl-2-methyl-4-oxo-pyrrolidine-3-carboxylate (10.0 g) as brown oil.

Step 4: Preparation of 1-benzyl-5-methyl-pyrrolidin-3-one

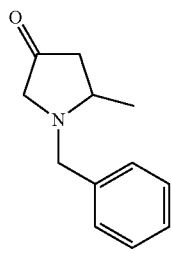

A mixture of methyl 1-benzyl-2-methyl-4-oxo-pyrrolidine-3-carboxylate (10.0 g, 40.44 mmol) and aqueous solution of H₂SO₄ (5%, prepared with 20.0 g con.H₂SO₄ and 380 mL water) was heated under reflux for 28 hrs. After being cooled to rt, the resulting mixture was neutralized with solid Na₂CO₃ and extracted with EA (100 mL) for three times. The combined organic layer was dried over anhydrous Na₂SO₄ and concentrated in vacuo. The residue was purified by column (eluting with PE/EA=10/1, v:v) to give 1-benzyl-5-methyl-pyrrolidin-3-one (5.4 g) as yellow oil.

Step 5: Preparation of tert-butyl 2-methyl-4-oxo-pyrrolidine-1-carboxylate

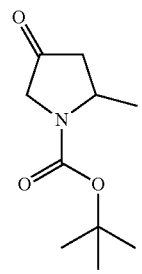

To a solution of 1-benzyl-5-methyl-pyrrolidin-3-one (5.4 g, 28.5 mmol) and Boc₂O (7.5 g, 34.4 mmol) in EtOH (50 mL) was added Pd/C (0.8 g, 10 wt %). The resulting mixture was stirred under H₂ (40 Psi) atmosphere at rt for 16 hrs and then filtered. The filtrate was concentrated in vacuo. The residue was purified by column (eluting with PE/EA=20/1, v/v) to give tert-butyl 2-methyl-4-oxo-pyrrolidine-1-carboxylate (3.9 g) as colorless oil.

Step 6: Preparation of tert-butyl 5-methyl-2-pyrimidin-2-yl-5,7-dihydropyrrolo[3,4-d]pyrimidine-6-carboxylate

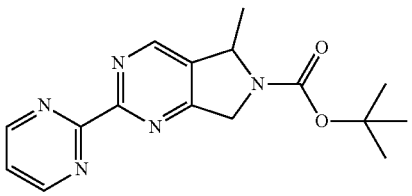 [SMILES: CC1c2cnc(-c3ncccn3)nc2CN1C(=O)OC(C)(C)C]

A mixture of tert-butyl 2-methyl-4-oxo-pyrrolidine-1-carboxylate (1.0 g, 5.0 mmol) and DMFDMA (10 mL) was heated at 120° C. with stirring 12 hrs under N₂. The resulting reaction mixture was concentrated in vacuo and the residue was dissolved in EtOH (18 mL). To the solution was added pyrimidine-2-carboximidamide hydrochloride (1.45 g, 5.6 mmol) and K₂CO₃ (2.57 g, 18.6 mmol). The resulting mixture was heated at 60° C. with stirring for 2 hrs under N₂, was and then concentrated in vacuo. The residue was purified by prep-HPLC to give tert-butyl 5-methyl-2-pyrimidin-2-yl-5,7-dihydropyrrolo[3,4-d]pyrimidine-6-carboxylate (628 mg) as red oil.

Step 7: Preparation of 5-methyl-2-pyrimidin-2-yl-6,7-dihydro-5H-pyrrolo[3,4-d]pyrimidine hydrochloride

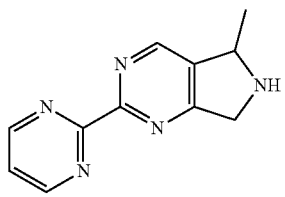 [SMILES: CC1NCc2nc(-c3ncccn3)ncc21]

A mixture of tert-butyl 5-methyl-2-pyrimidin-2-yl-5,7-dihydropyrrolo[3,4-d]pyrimidine-6-carboxylate (2.26 g, 7.21 mmol) and a solution of 1M HCl in EA (30 mL, 30 mmol) in MeOH (10 mL) was stirred at rt overnight. The resulting mixture was concentrated in vacuo to afford crude 5-methyl-2-pyrimidin-2-yl-6,7-dihydro-5H-pyrrolo[3,4-d]pyrimidine hydrochloride (2.02 g) as a yellow solid, which was used in the next step without any further purification.

Step 8: Preparation of (5-methyl-2-pyrimidin-2-yl-5,7-dihydropyrrolo[3,4-d]pyrimidin-6-yl)-(5-methyl-thiazol-2-yl)methanone

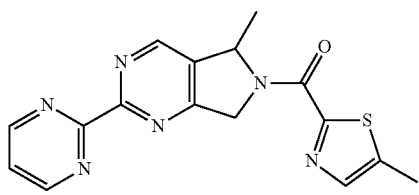 [SMILES: Cc1cnc(C(=O)N2Cc3nc(-c4ncccn4)ncc3C2C)s1]

A mixture of 5-methyl-2-(pyrimidin-2-yl)-6,7-dihydro-5H-pyrrolo[3,4-d]pyrimidine hydrochloride (56.1 mg, 0.2 mmol), 5-methylthiazole-2-carboxylic acid (28.6 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified prep-HPLC to afford (5-methyl-2-pyrimidin-2-yl-5,7-dihydropyrrolo[3,4-d]pyrimidin-6-yl)-(5-methylthiazol-2-yl)methanone (17 mg) as a yellow solid. $^1$H NMR (400 MHz, CDCl$_3$) δ ppm: 9.00 (d, 2H), 8.92-8.82 (m, 1H), 7.60-7.53 (m, 1H), 7.42 (t, 1H), 6.70-5.73 (m, 1H), 5.70-4.93 (m, 2H), 2.52-2.45 (m, 3H), 1.68-1.55 (m, 3H). MS obsd. (ESI$^+$) [(M+H)$^+$]: 339.

Example 2

(5-Methoxy-2-thienyl)-(5-methyl-2-pyrimidin-2-yl-5,7-dihydropyrrolo[3,4-d]pyrimidin-6-yl)methanone

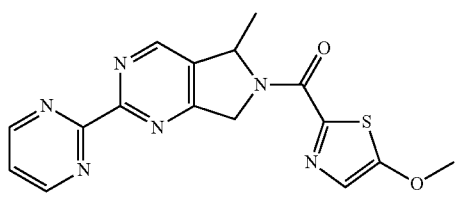 [SMILES: COc1cnc(C(=O)N2Cc3nc(-c4ncccn4)ncc3C2C)s1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 5-methoxythiophene-2-carboxylic acid (31.6 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (5-methoxy-2-thienyl)-(5-methyl-2-pyrimidin-2-yl-5,7-dihydropyrrolo[3,4-d]pyrimidin-6-yl)methanone (17 mg) as a yellow solid. $^1$H NMR (400 MHz, CDCl$_3$) δ ppm: 9.02 (d, 2H), 8.90 (s, 1H), 7.45 (t, 1H), 7.31-7.24 (m, 1H), 6.21 (d, 1H), 5.78 (m, 1H), 5.28-5.14 (m, 2H), 4.05-3.85 (m, 3H), 1.63 (d, 3H). MS obsd. (ESI$^+$) [(M+H)$^+$]: 354.

Example 3

(5-Methyl-2-pyrimidin-2-yl-5,7-dihydropyrrolo[3,4-d]pyrimidin-6-yl)-[4-(trifluoromethyl)-2-thienyl]methanone

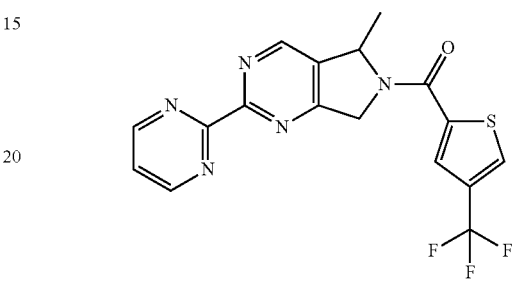

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 4-(trifluoromethyl)thiazole-2-carboxylic acid (39.4 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (5-methyl-2-pyrimidin-2-yl-5,7-dihydropyrrolo[3,4-d]pyrimidin-6-yl)[4-(trifluoromethyl)-2-thienyl]methanone (16 mg) as a yellow solid. $^1$H NMR (400 MHz, CDCl$_3$) δ ppm: 9.01 (d, 2H), 8.95-8.87 (m, 1H), 8.00-7.91 (m, 1H), 7.43 (t, 1H), 6.58-5.73 (m, 1H), 5.72-4.95 (m, 2H), 1.70 (d, 3H). MS obsd. (ESI$^+$) [(M+H)$^+$]: 392.

Example 4

(3-Fluoro-5-methoxy-phenyl)-(5-methyl-2-pyrimidin-2-yl-5,7-dihydropyrrolo[3,4-d]pyrimidin-6-yl)methanone

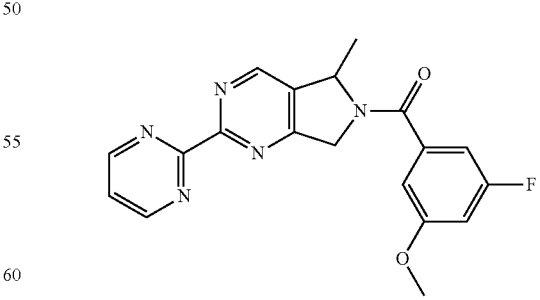

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 3-fluoro-5-methoxybenzoic acid (34 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (3-fluoro-5-methoxy-phenyl)-(5-methyl-2-pyrimidin-2-yl-5,7-dihydropyrrolo[3,4-d]pyrimidin-6-yl)methanone (19 mg) as a yellow solid. $^1$H NMR (400 MHz, CDCl₃) δ ppm: 9.06-8.80 (m, 3H), 7.43-7.33 (m, 1H), 6.87-6.75 (m, 2H), 6.68 (td, 1H), 5.81-5.28 (m, 1H), 5.04-4.69 (m, 2H), 3.78 (s, 3H), 1.56-1.75 (m, 2H). MS obsd. (ESI⁺) [(M+H)⁺]: 366.

Example 5

(5-Methyl-2-pyrimidin-2-yl-5,7-dihydropyrrolo[3,4-d]pyrimidin-6-yl)-(2-thienyl)methanone

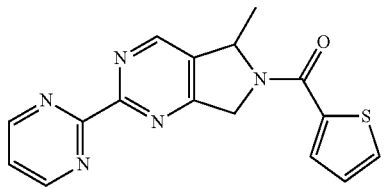 [SMILES: CC1c2cnc(-c3ncccn3)nc2CN1C(=O)c1cccs1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), thiophene-2-carboxylic acid (25.6 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (5-methyl-2-pyrimidin-2-yl-5,7-dihydropyrrolo[3,4-d]pyrimidin-6-yl)-(2-thienyl)methanone (19 mg) as a yellow solid. $^1$H NMR (400 MHz, CDCl₃) δ ppm: 8.99 (d, 2H), 8.89 (s, 1H), 7.59 (dd, 1H), 7.52 (dd, 1H), 7.41 (t, 1H), 7.10 (dd, 1H), 5.79 (q, 1H), 5.24 (s, 2H), 1.65 (br d, 3H). MS obsd. (ESI⁺) [(M+H)⁺]: 324.

Example 6

(5-Methyl-2-pyrimidin-2-yl-5,7-dihydropyrrolo[3,4-d]pyrimidin-6-yl)-(4-methyl-2-thienyl)methanone

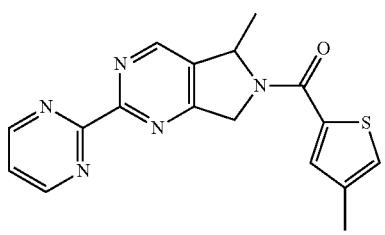 [SMILES: Cc1csc(C(=O)N2Cc3nc(-c4ncccn4)ncc3C2C)c1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 4-methylthiophene-2-carboxylic acid (28.4 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (5-methyl-2-pyrimidin-2-yl-5,7-dihydropyrrolo[3,4-d]pyrimidin-6-yl)-(4-methyl-2-thienyl)methanone (15 mg) as a yellow solid. $^1$H NMR (400 MHz, CDCl₃) δ ppm: 9.02 (d, 2H), 8.90 (s, 1H), 7.45 (t, 1H), 7.43-7.26 (m, 1H), 7.11 (s, 1H), 5.83-5.72 (m, 1H), 5.30-5.16 (m, 2H), 2.28-2.16 (m, 3H), 1.68-1.59 (m, 3H). MS obsd. (ESI⁺) [(M+H)⁺]: 338.

Example 7

(4-Bromo-2-thienyl)-(5-methyl-2-pyrimidin-2-yl-5,7-dihydropyrrolo[3,4-d]pyrimidin-6-yl)methanone

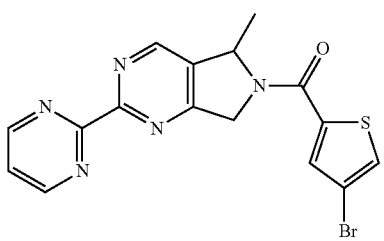 [SMILES: CC1c2cnc(-c3ncccn3)nc2CN1C(=O)c1cc(Br)cs1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 4-bromothiophene-2-carboxylic acid (41.4 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (4-bromo-2-thienyl)-(5-methyl-2-pyrimidin-2-yl-5,7-dihydropyrrolo[3,4-d]pyrimidin-6-yl)methanone (22 mg) as a yellow solid. $^1$H NMR (400 MHz, CDCl₃) δ ppm: 9.00 (d, 2H), 8.90 (s, 1H), 7.46 (d, 1H), 7.45-7.41 (m, 2H), 5.77 (q, 1H), 5.22 (d, 2H), 1.65 (br d, 3H). MS obsd. (ESI⁺) [(M+H)⁺]: 402.

Example 8

(5-Methyl-2-pyrimidin-2-yl-5,7-dihydropyrrolo[3,4-d]pyrimidin-6-yl)-(5-methyl-2-thienyl)methanone

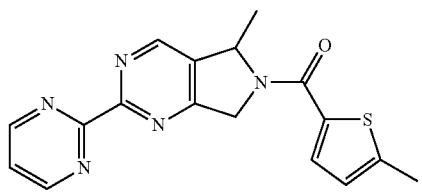 [SMILES: Cc1ccc(C(=O)N2Cc3nc(-c4ncccn4)ncc3C2C)s1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 5-methylthiophene-2-carboxylic acid (28.4 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (5-methyl-2-pyrimidin-2-yl-5,7-dihydropyrrolo[3,4-d]pyrimidin-6-yl)-(5-methyl-2-thienyl)methanone (15 mg) as a yellow solid. $^1$H NMR (400 MHz, CDCl$_3$) δ ppm: 9.01 (d, 2H), 8.89 (s, 1H), 7.43 (t, 1H), 7.39 (d, 1H), 6.76 (dd, 1H), 5.78 (q, 1H), 5.27-5.15 (m, 2H), 2.48 (s, 3H), 1.63 (d, 3H). MS obsd. (ESI$^+$) [(M+H)$^+$]: 338.

Example 9

(5-Chloro-2-thienyl)-(5-methyl-2-pyrimidin-2-yl-5,7-dihydropyrrolo[3,4-d]pyrimidin-6-yl)methanone

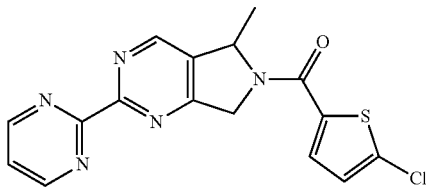 [SMILES: CC1c2cnc(-c3ncccn3)nc2CN1C(=O)c1ccc(Cl)s1]

A mixture of 5-methyl-2-(pyrimidin-2-yl)-6,7-dihydro-5H-pyrrolo[3,4-d]pyrimidine hydrochloride (the product of step 7 in Example 1, 56.1 mg, 0.2 mmol), 5-chlorothiophene-2-carboxylic acid (32.5 mg, 0.2 mmol), HATU (76 mg, 0.2 mmol) and DIPEA (77.5 mg, 0.6 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (5-chloro-2-thienyl)-(5-methyl-2-pyrimidin-2-yl-5,7-dihydropyrrolo[3,4-d]pyrimidin-6-yl)methanone (11 mg) as a yellow solid. $^1$H NMR (400 MHz, CDCl$_3$) δ ppm: 9.00 (d, 2H), 8.89 (s, 1H), 7.43 (t, 1H), 7.34 (d, 1H), 6.93 (d, 1H), 5.76 (q, 1H), 5.25-5.13 (m, 2H), 1.64 (d, 3H). MS obsd. (ESI$^+$) [(M+H)$^+$]: 358.

Example 10

(4,5-Dimethylthiazol-2-yl)-(5-methyl-2-pyrimidin-2-yl-5,7-dihydropyrrolo[3,4-d]pyrimidin-6-yl)methanone

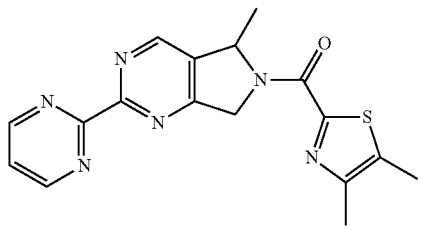 [SMILES: Cc1nc(C(=O)N2Cc3nc(-c4ncccn4)ncc3C2C)sc1C]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 4,5-dimethylthiazole-2-carboxylic acid (15.7 mg, 0.1 mmol), HATU (38 mg, 0.1 mmol) and DIPEA (38.8 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (4,5-dimethylthiazol-2-yl)-(5-methyl-2-pyrimidin-2-yl-5,7-dihydropyrrolo[3,4-d]pyrimidin-6-yl)methanone (14 mg) as a yellow solid. $^1$H NMR (400 MHz, CDCl$_3$) δ ppm: 9.10-8.76 (m, 3H), 7.49-7.34 (m, 1H), 6.65-5.70 (m, 1H), 5.70-4.90 (m, 2H), 2.41-2.28 (m, 6H), 1.72-1.63 (m, 3H). MS obsd. (ESI$^+$) [(M+H)$^+$]: 353.

Example 11

(1-Methylpyrazol-4-yl)-(5-methyl-2-pyrimidin-2-yl-5,7-dihydropyrrolo[3,4-d]pyrimidin-6-yl)methanone

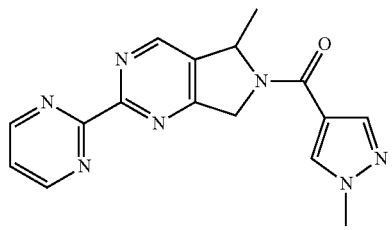 [SMILES: CC1c2cnc(-c3ncccn3)nc2CN1C(=O)c1cnn(C)c1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 1-methyl-1H-pyrazole-4-carboxylic acid (12.6 mg, 0.1 mmol), HATU (38 mg, 0.1 mmol) and DIPEA (38.8 mg, 0.3 mmol) in DMF (1 mL) was stirred at rt for 1 hr. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (1-methylpyrazol-4-yl)-(5-methyl-2-pyrimidin-2-yl-5,7-dihydropyrrolo[3,4-d]pyrimidin-6-yl)methanone (12 mg) as a yellow solid. $^1$H NMR (400 MHz, CDCl$_3$) δ ppm: 9.08 (br d, 2H), 8.97 (s, 1H), 7.95 (s, 1H), 7.90 (s, 1H), 7.51 (t, 1H), 5.90-5.75 (m, 1H), 5.24 (br s, 2H), 4.00 (s, 3H), 1.77-1.72 (m, 3H). MS obsd. (ESI$^+$) [(M+H)$^+$]: 322.

Example 12

(1-Methylindazol-3-yl)-(5-methyl-2-pyrimidin-2-yl-5,7-dihydropyrrolo[3,4-d]pyrimidin-6-yl)methanone

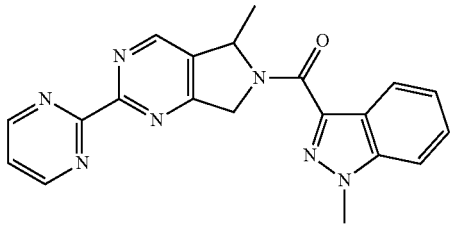 [SMILES: CC1c2cnc(-c3ncccn3)nc2CN1C(=O)c1nn(C)c2ccccc12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 1-methyl-1H-indazole-3-carboxylic acid (17.6 mg, 0.1 mmol), HATU (38 mg, 0.1 mmol) and DIPEA (38.8 mg, 0.3 mmol) in DMF (1 mL) was stirred at rt for 1 hr. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (1-methylindazol-3-yl)-(5-methyl-2-pyrimidin-2-yl-5,7-dihydropyrrolo[3,4-d]pyrimidin-6-yl)methanone (13 mg) as a yellow solid. $^1$H NMR (400 MHz, CDCl₃) δ ppm: 9.08-8.84 (m, 3H), 8.36 (d, 1H), 7.46-7.36 (m, 3H), 7.30-7.22 (m, 1H), 6.66-5.80 (m, 1H), 5.70-5.01 (m, 2H), 4.17-4.03 (m, 3H), 1.73-1.50 (m, 3H). MS obsd. (ESI⁺) [(M+H)⁺]: 372.

Example 13

(1-Methylpyrazol-3-yl)-(5-methyl-2-pyrimidin-2-yl-5,7-dihydropyrrolo[3,4-d]pyrimidin-6-yl)methanone

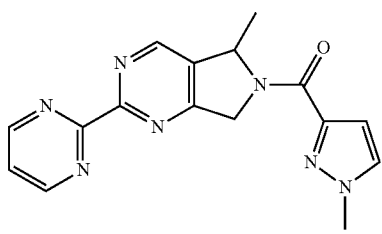 [SMILES: CC1c2cnc(-c3ncccn3)nc2CN1C(=O)c1ccn(C)n1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 1-methyl-1H-pyrazole-3-carboxylic acid (12.6 mg, 0.1 mmol), HATU (38 mg, 0.1 mmol) and DIPEA (38.8 mg, 0.3 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (1-methylpyrazol-3-yl)-(5-methyl-2-pyrimidin-2-yl-5,7-dihydropyrrolo[3,4-d]pyrimidin-6-yl)methanone (13 mg) as a yellow solid. $^1$H NMR (400 MHz, CDCl₃) δ ppm: 9.20-8.95 (m, 3H), 7.60-7.53 (m, 1H), 7.51-7.41 (m, 1H), 6.95-6.90 (m, 1H), 6.60-5.80 (m, 1H), 5.73-5.03 (m, 2H), 4.05-3.94 (m, 3H), 1.82-1.71 (m, 3H). MS obsd. (ESI⁺) [(M+H)⁺]: 322.

Example 14

1H-Benzimidazol-2-yl-(5-methyl-2-pyrimidin-2-yl-5,7-dihydropyrrolo[3,4-d]pyrimidin-6-yl)methanone

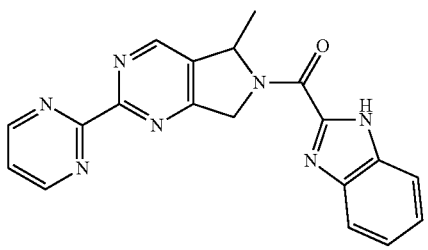 [SMILES: CC1c2cnc(-c3ncccn3)nc2CN1C(=O)c1nc2ccccc2[nH]1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), H-benzo[d]imidazole-2-carboxylic acid (16.2 mg, 0.1 mmol), HATU (38 mg, 0.1 mmol) and DIPEA (38.8 mg, 0.3 mmol) in DMF (1 mL) was stirred at rt for 64 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford 1H-benzimidazol-2-yl-(5-methyl-2-pyrimidin-2-yl-5,7-dihydropyrrolo[3,4-d]pyrimidin-6-yl)methanone (17 mg) as a yellow solid. $^1$H NMR (400 MHz, DMSO-d6) δ ppm: 13.35-13.26 (m, 1H), 9.16-9.06 (m, 1H), 9.03 (d, 2H), 7.89-7.27 (m, 5H), 6.81-5.73 (m, 1H), 5.72-4.95 (m, 2H), 1.74-1.59 (m, 3H). MS obsd. (ESI⁺) [(M+H)⁺]: 358.

Example 15

(4-Methoxyphenyl)-(5-methyl-2-pyrimidin-2-yl-5,7-dihydropyrrolo[3,4-d]pyrimidin-6-yl)methanone

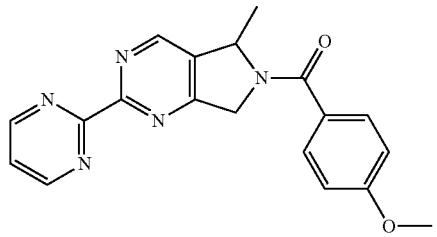 [SMILES: COc1ccc(C(=O)N2Cc3nc(-c4ncccn4)ncc3C2C)cc1]

To a mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol) and TEA (30.4 mg, 0.3 mmol) in DCM (1 mL) was added 4-methoxybenzoyl chloride (17.1 mg, 0.1 mmol) at 0° C. The resulting mixture was warmed to rt and stirred for 20 hrs, then diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford (4-methoxyphenyl)-(5-methyl-2-pyrimidin-2-yl-5,7-dihydropyrrolo[3,4-d]pyrimidin-6-yl)methanone (14 mg) as a yellow solid. $^1$H NMR (400 MHz, CDCl₃) δ ppm: 9.08 (d, 2H), 8.94 (br s, 1H), 7.60 (br d, 2H), 7.52 (t, 1H), 6.97 (d, 2H), 5.86 (br s, 1H), 5.20-5.09 (m, 1H), 4.94 (br s, 1H), 3.88 (s, 3H), 1.70 (br s, 3H). MS obsd. (ESI⁺) [(M+H)⁺]: 348.

Example 16

(1-Ethylpyrazol-3-yl)-(5-methyl-2-pyrimidin-2-yl-5,7-dihydropyrrolo[3,4-d]pyrimidin-6-yl)methanone

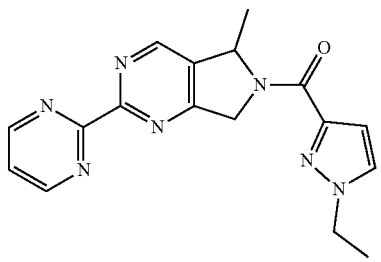 [SMILES: CCn1ccc(C(=O)N2Cc3nc(-c4ncccn4)ncc3C2C)n1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 1-ethyl-1H-pyrazole-3-carboxylic acid (14 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with $H_2O$ (20 mL) and extracted with DCM (30 mL) for three times. The combined organic layer was washed with brine, dried over anhydrous $Na_2SO_4$ and concentrated in vacuo. The residue was purified by prep-HPLC to afford (1-ethylpyrazol-3-yl)-(5-methyl-2-pyrimidin-2-yl-5,7-dihydropyrrolo[3,4-d]pyrimidin-6-yl)methanone (17 mg) as a yellow solid. $^1$H NMR (400 MHz, CDCl$_3$) δ ppm: 9.07 (d, 2H), 8.98-8.90 (m, 1H), 7.52-7.41 (m, 2H), 6.95-6.88 (m, 1H), 6.55-5.78 (m, 1H), 5.70-4.99 (m, 2H), 4.32-4.12 (m, 2H), 1.74 (d, 3H), 1.56 (t, 3H). MS obsd. (ESI$^+$) [(M+H)$^+$]: 336.

Example 17

(5-Bromo-2-thienyl)-(5-methyl-2-pyrimidin-2-yl-5,7-dihydropyrrolo[3,4-d]pyrimidin-6-yl)methanone

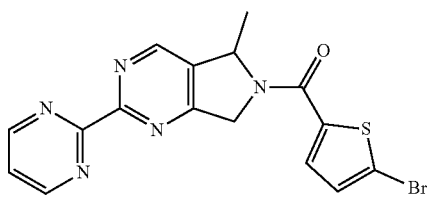 [SMILES: CC1c2cnc(-c3ncccn3)nc2CN1C(=O)c1ccc(Br)s1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 5-bromothiophene-2-carboxylic acid (20.7 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with $H_2O$ (20 mL) and extracted with DCM (30 mL) for three times. The combined organic layer was washed with brine, dried over anhydrous $Na_2SO_4$ and concentrated in vacuo. The residue was purified by prep-HPLC to afford (5-bromo-2-thienyl)-(5-methyl-2-pyrimidin-2-yl-5,7-dihydropyrrolo[3,4-d]pyrimidin-6-yl)methanone (10 mg) as an off-white solid. $^1$H NMR (400 MHz, DMSO-d6) δ ppm: 9.08-8.97 (m, 3H), 7.71-7.61 (m, 2H), 7.38 (d, 1H), 5.72-5.57 (m, 1H), 5.41 (br d, 1H), 5.18 (br d, 1H), 1.59 (d, 3H). MS obsd. (ESI$^+$) [(M+H)$^+$]: 402.

Example 18

(5-Methyl-2-pyrimidin-2-yl-5,7-dihydropyrrolo[3,4-d]pyrimidin-6-yl)-(5-nitro-2-thienyl)methanone

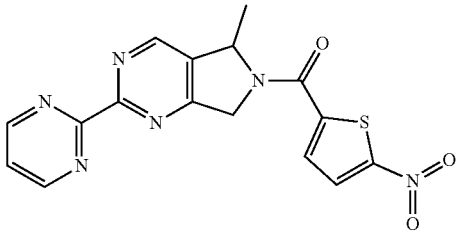 [SMILES: CC1c2cnc(-c3ncccn3)nc2CN1C(=O)c1ccc([N+](=O)[O-])s1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 5-nitrothiophene-2-carboxylic acid (17.3 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with $H_2O$ (20 mL) and extracted with DCM (30 mL) for three times. The combined organic layer was washed with brine, dried over anhydrous $Na_2SO_4$ and concentrated in vacuo. The residue was purified by prep-HPLC to afford (5-methyl-2-pyrimidin-2-yl-5,7-dihydropyrrolo[3,4-d]pyrimidin-6-yl)-(5-nitro-2-thienyl)methanone (11 mg) as a yellow solid. $^1$H NMR (400 MHz, DMSO-d6) δ ppm: 9.11-8.96 (m, 3H), 8.19 (d, 1H), 7.87 (d, 1H), 7.66 (t, 1H), 6.05-5.60 (m, 1H), 5.55-4.95 (m, 2H), 1.72-1.40 (m, 3H). MS obsd. (ESI$^+$) [(M+H)$^+$]: 369.

Example 19

(5-Methyl-2-pyrimidin-2-yl-5,7-dihydropyrrolo[3,4-d]pyrimidin-6-yl)-(2-naphthyl)methanone

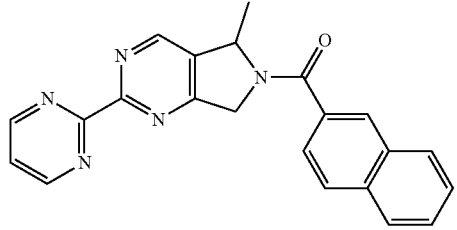 [SMILES: CC1c2cnc(-c3ncccn3)nc2CN1C(=O)c1ccc2ccccc2c1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 2-naphthoic acid (17.2 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with $H_2O$ (20 mL) and extracted with DCM (30 mL) for three times. The combined organic layer was washed with brine, dried over anhydrous $Na_2SO_4$ and concentrated in vacuo. The residue was purified by prep-HPLC to afford (5-methyl-2-pyrimidin-2-yl-5,7-dihydropyrrolo[3,4-d]pyrimidin-6-yl)-(2-naphthyl)methanone (7 mg) as an off-white solid. $^1$H NMR (400 MHz, DMSO-d6) δ ppm: 9.14-8.91 (m, 3H), 8.37-7.97 (m, 4H), 7.80-7.57 (m, 4H), 5.81-5.57 (m, 1H), 5.41-4.65 (m, 2H), 1.82-1.18 (m, 3H). MS obsd. (ESI+) [(M+H)+]: 368.

Example 20

Imidazo[1,2-a]pyridin-2-yl-(5-methyl-2-pyrimidin-2-yl-5,7-dihydropyrrolo[3,4-d]pyrimidin-6-yl)methanone

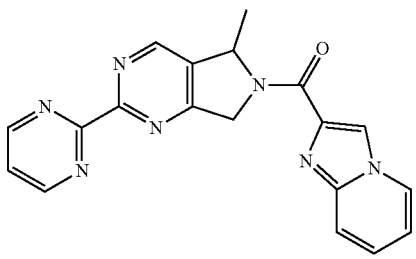 [SMILES: CC1c2cnc(-c3ncccn3)nc2CN1C(=O)c1cn2ccccc2n1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), imidazo[1,2-a]pyridine-2-carboxylic acid (16.2 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford imidazo[1,2-a]pyridin-2-yl-(5-methyl-2-pyrimidin-2-yl-5,7-dihydropyrrolo[3,4-d]pyrimidin-6-yl)methanone (9 mg) as a yellow solid. $^1$H NMR (400 MHz, DMSO-d6) δ ppm: 9.17-8.95 (m, 3H), 8.67-8.48 (m, 2H), 7.77-7.29 (m, 3H), 7.08-6.66 (m, 1H), 5.74-4.91 (m, 3H), 1.71-1.47 (m, 3H). MS obsd. (ESI+) [(M+H)+]: 358.

Example 21

(3-Methylbenzofuran-2-yl)-(5-methyl-2-pyrimidin-2-yl-5,7-dihydropyrrolo[3,4-d]pyrimidin-6-yl)methanone

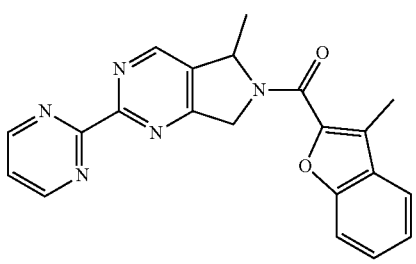 [SMILES: Cc1c(C(=O)N2Cc3nc(-c4ncccn4)ncc3C2C)oc2ccccc12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 3-methylbenzofuran-2-carboxylic acid (17.6 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (3-methylbenzofuran-2-yl)-(5-methyl-2-pyrimidin-2-yl-5,7-dihydropyrrolo[3,4-d]pyrimidin-6-yl)methanone (8 mg) as an off-white solid. $^1$H NMR (400 MHz, DMSO-d6) δ ppm: 9.25-8.83 (m, 3H), 7.94-7.26 (m, 5H), 6.25-5.63 (m, 1H), 5.60-4.90 (m, 2H), 2.51 (s, 3H), 1.73-1.38 (m, 3H). MS obsd. (ESI+) [(M+H)+]: 372.

Example 22

(6-Methoxypyrazin-2-yl)-(5-methyl-2-pyrimidin-2-yl-5,7-dihydropyrrolo[3,4-d]pyrimidin-6-yl)methanone

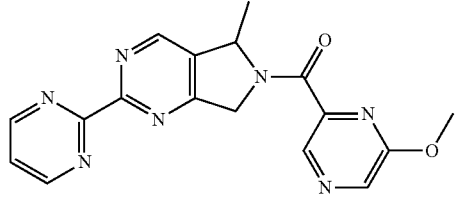 [SMILES: COc1cncc(C(=O)N2Cc3nc(-c4ncccn4)ncc3C2C)n1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 6-methoxypyrazine-2-carboxylic acid (15.4 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (6-methoxypyrazin-2-yl)-(5-methyl-2-pyrimidin-2-yl-5,7-dihydropyrrolo[3,4-d]pyrimidin-6-yl)methanone (7 mg) as a yellow solid. $^1$H NMR (400 MHz, DMSO-d6) δ ppm: 9.04-8.91 (m, 3H), 8.67-8.55 (m, 1H), 8.51-8.41 (m, 1H), 7.64-7.56 (m, 1H), 6.15-5.62 (m, 1H), 5.47-4.89 (m, 2H), 4.01-3.96 (m, 3H), 1.63-1.28 (m, 3H). MS obsd. (ESI+) [(M+H)+]: 350.

Example 23

1H-indazol-3-yl-(5-methyl-2-pyrimidin-2-yl-5,7-dihydropyrrolo[3,4-d]pyrimidin-6-yl)methanone

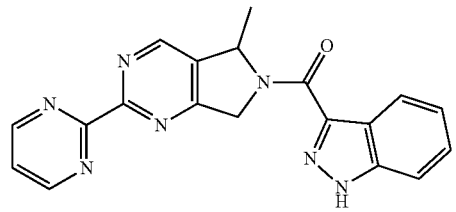 [SMILES: CC1c2cnc(-c3ncccn3)nc2CN1C(=O)c1n[nH]c2ccccc12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), 1H-indazole-3-carboxylic acid (16.2 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford 1H-indazol-3-yl-(5-methyl-2-pyrimidin-2-yl-5,7-dihydropyrrolo[3,4-d]pyrimidin-6-yl)methanone (5 mg) as a yellow solid. $^1$H NMR (400 MHz, DMSO-d6) δ ppm: 13.72 (br s, 1H), 9.04-8.91 (m, 3H), 8.22-8.11 (m, 1H), 7.67-7.54 (m, 2H), 7.44-7.34 (m, 1H), 7.21 (t, 1H), 6.43-5.64 (m, 1H), 5.49-4.87 (m, 2H), 1.64-1.43 (m, 3H). MS obsd. (ESI$^+$) [(M+H)$^+$]: 358.

Example 24

(5-Methyl-2-pyrimidin-2-yl-5,7-dihydropyrrolo[3,4-d]pyrimidin-6-yl)-pyrazolo[1,5-a]pyridin-3-yl-methanone

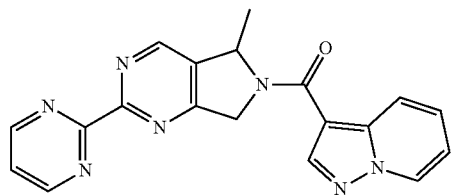 [SMILES: CC1c2cnc(-c3ncccn3)nc2CN1C(=O)c1cnn2ccccc12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), pyrazolo[1,5-a]pyridine-3-carboxylic acid (16.2 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford (5-methyl-2-pyrimidin-2-yl-5,7-dihydropyrrolo[3,4-d]pyrimidin-6-yl)-pyrazolo[1,5-a]pyridin-3-yl-methanone (10 mg) as a yellow solid. $^1$H NMR (400 MHz, DMSO-d6) δ ppm: 9.06-8.90 (m, 3H), 8.84-8.72 (m, 1H), 8.60 (s, 1H), 8.21 (d, 1H), 7.60 (t, 1H), 7.46 (ddd, 1H), 7.07 (dt, 1H), 5.70 (br s, 1H), 5.53-4.97 (m, 2H), 1.55 (br d, 3H). MS obsd. (ESI$^+$) [(M+H)$^+$]: 358.

Example 25

1,3-Benzothiazol-6-yl-(5-methyl-2-pyrimidin-2-yl-5,7-dihydropyrrolo[3,4-d]pyrimidin-6-yl)methanone

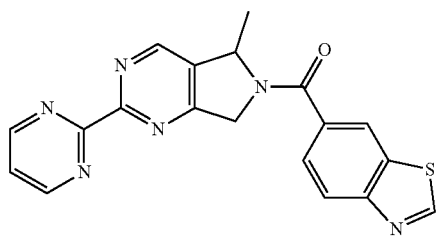 [SMILES: CC1c2cnc(-c3ncccn3)nc2CN1C(=O)c1ccc2ncsc2c1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), benzo[d]thiazole-6-carboxylic acid (17.9 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford 1,3-benzothiazol-6-yl-(5-methyl-2-pyrimidin-2-yl-5,7-dihydropyrrolo[3,4-d]pyrimidin-6-yl)methanone (10 mg) as a yellow solid. $^1$H NMR (400 MHz, DMSO-d6) δ ppm: 9.54 (s, 1H), 9.10-8.91 (m, 3H), 8.54 (br s, 1H), 8.19 (br d, 1H), 7.87-7.59 (m, 2H), 5.80-5.50 (m, 1H), 5.36-4.66 (m, 2H), 1.75-1.10 (m, 3H). MS obsd. (ESI$^+$) [(M+H)$^+$]: 375.

Example 26

Imidazo[1,2-a]pyridin-3-yl-(5-methyl-2-pyrimidin-2-yl-5,7-dihydropyrrolo[3,4-d]pyrimidin-6-yl)methanone

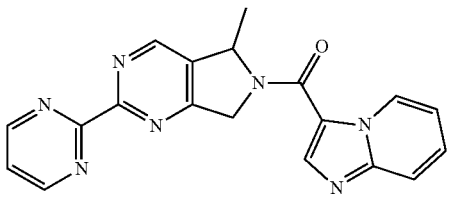 [SMILES: CC1c2cnc(-c3ncccn3)nc2CN1C(=O)c1cnc2ccccn12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), imidazo[1,2-a]pyridine-3-carboxylic acid (16.2 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford imidazo[1,2-a]pyridin-3-yl-(5-methyl-2-pyrimidin-2-yl-5,7-dihydropyrrolo[3,4-d]pyrimidin-6-yl)methanone (10 mg) as a pink solid. $^1$H NMR (400 MHz, DMSO-d6) δ ppm: 9.42 (br d, 1H), 9.13-8.97 (m, 3H), 8.63 (s, 1H), 7.88 (d, 1H), 7.76-7.62 (m, 2H), 7.31 (t, 1H), 5.90-5.78 (m, 1H), 5.55-5.16 (m, 2H), 1.65 (br d, 3H). MS obsd. (ESI$^+$) [(M+H)$^+$]: 358.

Example 27

1,2-Benzoxazol-3-yl-(5-methyl-2-pyrimidin-2-yl-5,7-dihydropyrrolo[3,4-d]pyrimidin-6-yl)methanone

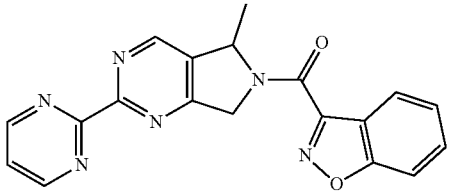 [SMILES: CC1c2cnc(-c3ncccn3)nc2CN1C(=O)c1noc2ccccc12]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), benzo[d]isoxazole-3-carboxylic acid (16.3 mg, 0.1 mmol), HATU (38 mg, 0.1 mmol) and TEA (30.4 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford 1,2-benzoxazol-3-yl-(5-methyl-2-pyrimidin-2-yl-5,7-dihydropyrrolo[3,4-d]pyrimidin-6-yl)methanone (6 mg) as a yellow solid. $^1$H NMR (400 MHz, DMSO-d6) δ ppm: 9.16-8.94 (m, 3H), 8.10-8.00 (m, 1H), 7.88-7.78 (m, 1H), 7.68 (t, 1H), 7.55 (dd, 1H), 7.33 (dd, 1H), 6.32-5.72 (m, 1H), 5.64-5.01 (m, 2H), 1.76-1.50 (m, 3H). MS obsd. (ESI$^+$) [(M+H)$^+$]: 359.

Example 28

1,3-Benzothiazol-2-yl-(5-methyl-2-pyrimidin-2-yl-5,7-dihydropyrrolo[3,4-d]pyrimidin-6-yl)methanone

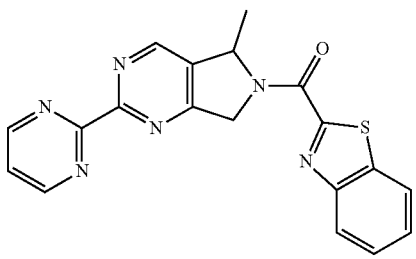 [SMILES: CC1c2cnc(-c3ncccn3)nc2CN1C(=O)c1nc2ccccc2s1]

A mixture of 5-methyl-2-(pyrimidin-2-yl)-6,7-dihydro-5H-pyrrolo[3,4-d]pyrimidine hydrochloride (the product of step 7 in Example 1, 28.1 mg, 0.1 mmol), benzo[d]thiazole-2-carboxylic acid (17.9 mg, 0.1 mmol), HATU (38 mg, 0.1 mmol) and DIPEA (38.8 mg, 0.3 mmol) in DMF (1 mL) was stirred at rt for 64 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The residue was purified by prep-HPLC to afford 1,3-benzothiazol-2-yl-(5-methyl-2-pyrimidin-2-yl-5,7-dihydropyrrolo[3,4-d]pyrimidin-6-yl)methanone (6 mg) as a yellow solid. $^1$H NMR (400 MHz, DMSO-d6) δ ppm: 9.17-8.97 (m, 3H), 8.25 (d, 2H), 7.73-7.56 (m, 3H), 6.62-5.70 (m, 1H), 5.68-4.99 (m, 2H), 1.74-1.63 (m, 3H). MS obsd. (ESI$^+$) [(M+H)$^+$]: 375.

Example 29

6-(3,4-Difluoro-5-methoxy-phenyl)-2-(2-pyridyl)-5,7-dihydropyrrolo[3,4-d]pyrimidine

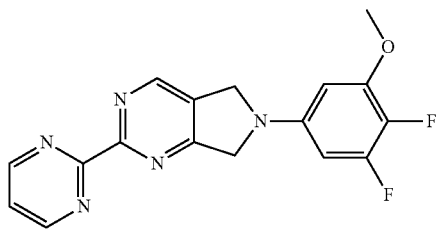 [SMILES: COc1cc(N2Cc3cnc(-c4ncccn4)nc3C2)cc(F)c1F]

Step 1: Preparation of benzyl 1,4-dioxa-7-azaspiro[4.4]nonane-7-carboxylate

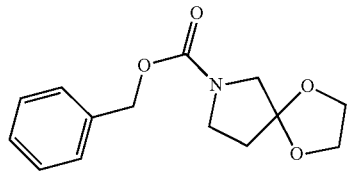 [SMILES: O=C(OCc1ccccc1)N1CCC2(C1)OCCO2]

A mixture of benzyl 3-oxopyrrolidine-1-carboxylate (20 g, 91.3 mmol), paraformaldehyde (17 g, 0.274 mol) and toluenesulfonic acid monohydrate (867 mg, 4.57 mmol) in toluene (200 mL) was heated under reflux with Dean-Stark apparatus for 36 hrs. After being cooled to rt, the resulting mixture was washed with saturated aqueous NaHCO$_3$ solution (200 mL) and brine, dried over anhydrous Na$_2$SO$_4$ and concentrated in vacuo. The residue was purified by column (eluting with PE/EA=5/1, v:v) to give benzyl 1,4-dioxa-7-azaspiro[4.4]nonane-7-carboxylate (15 g) as a colorless oil.

Step 2: Preparation of 1,4-dioxa-7-azaspiro[4.4]nonane

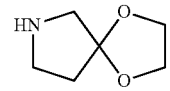

A solution of benzyl 1,4-dioxa-7-azaspiro[4.4]nonane-7-carboxylate (8 g, 30.4 mmol) in MeOH (80 mL) was stirred in the presence of Pd/C (0.5 g, 10 wt. %) under H$_2$ (30 Psi) at rt for 12 hrs. The mixture was filtered and the filtrate was concentrated in vacuo to give 1,4-dioxa-7-azaspiro[4.4]nonane (3 g) as a colorless oil, which was used in the next step without any further purification.

Step 3: Preparation of 7-(3,4-difluoro-5-methoxyphenyl)-1,4-dioxa-7-azaspiro[4.4]nonane

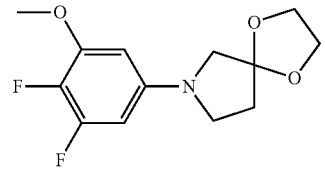 [SMILES: COc1cc(N2CCC3(C2)OCCO3)cc(F)c1F]

A mixture of 1,4-dioxa-7-azaspiro[4.4]nonane (2 g, 15.5 mmol), 5-bromo-1,2-difluoro-3-methoxy-benzene (4.47 g, 20.1 mmol), tert-BuONa (2.23 g, 23.25 mmol), Xantphos (325 mg) and Pd$_2$(dba)$_3$ (258 mg) in dioxane (20 mL) was heated at 100° C. with stirring under N$_2$ for 16 hrs. The resulting mixture was filtered and the filtrate was concentrated in vacuo. The residue was diluted with DCM (200 mL), then washed with water and brine, dried over Na$_2$SO$_4$ and concentrated in vacuo. The residue was purified by column (eluting with PE/EA=5/1, v:v) to give 7-(3,4-difluoro-5-methoxy-phenyl)-1,4-dioxa-7-azaspiro[4.4]nonane (2.7 g) as a yellow oil Step 4: Preparation of 1-(3,4-difluoro-5-methoxy-phenyl)pyrrolidin-3-one

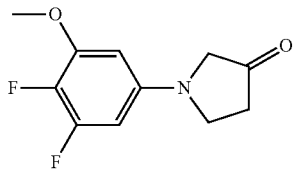 [SMILES: COc1cc(N2CCC(=O)C2)cc(F)c1F]

A mixture of 7-(3,4-difluoro-5-methoxy-phenyl)-1,4-dioxa-7-azaspiro[4.4]nonane (1 g, 3.7 mmol), formic acid (5 mL) and H₂O (5 mL) was heated at 90° C. with stirring for 2 hrs. After being cooled to rt, the resulting mixture was diluted with DCM, then washed with water, saturated aqueous NaHCO₃ and brine, dried over anhydrous Na₂SO₄ and concentrated in vacuo. The residue was purified by column (eluting with PE/EA=5/1, v:v) to give 1-(3,4-difluoro-5-methoxy-phenyl)pyrrolidin-3-one (350 mg) as a yellow solid.

Step 5: Preparation of 6-(3,4-difluoro-5-methoxy-phenyl)-2-(2-pyridyl)-5,7-dihydropyrrolo[3,4-d]pyrimidine

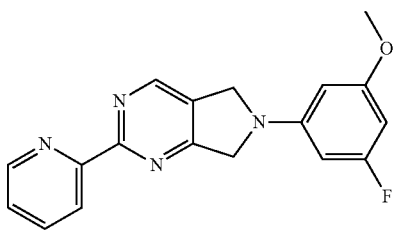 [SMILES: COc1cc(F)cc(N2Cc3cnc(-c4ccccn4)nc3C2)c1]

A mixture of 1-(3,4-difluoro-5-methoxy-phenyl)pyrrolidin-3-one (350 mg, 1.54 mmol) and DMFDMA (5 mL) was heated at 120° C. with stirring for 4 hrs. The resulting mixture was concentrated in vacuo and the residue was dissolved in MeOH (5 mL). To the solution was added pyridine-2-carboximidamide hydrochloride (246 mg, 1.56 mmol) and K₂CO₃ (474 mg, 3.43 mmol). The resulting mixture was heated at 60° C. with stirring for 16 hrs. After being cooled to rt, the resulting mixture was filtered and the filtrate was concentrated in vacuo. The residue was diluted with DCM (50 mL), then washed with brine, dried over anhydrous Na₂SO₄ and concentrated in vacuo. The residue was purified by prep-HPLC to give 6-(3,4-difluoro-5-methoxy-phenyl)-2-(2-pyridyl)-5,7-dihydropyrrolo[3,4-d]pyrimidine (10 mg) as a white solid. ¹H NMR (400 MHz, DMSO-d6) δ ppm: 3.93 (s, 3H), 4.73 (d, 4H), 6.24-6.37 (m, 2H), 7.49-7.60 (m, 1H), 8.00 (t, 1H), 8.39 (d, 1H), 8.76 (d, 1H), 8.98 (s, 1H). MS obsd. (ESI⁺) [(M+H)⁺]: 341.

Example 30

6-(6-Fluoro-4-methoxy-2-pyridyl)-5-methyl-2-pyrimidin-2-yl-5,7-dihydropyrrolo[3,4-d]pyrimidine

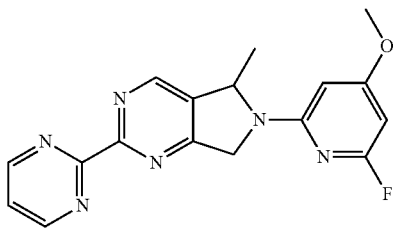 [SMILES: COc1cc(F)nc(N2Cc3nc(-c4ncccn4)ncc3C2C)c1]

Step 1: Preparation of 5-methyl-2-pyrimidin-2-yl-6,7-dihydro-5H-pyrrolo[3,4-d]pyrimidine

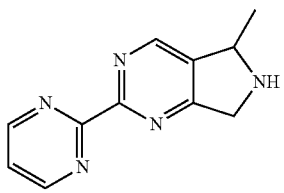 [SMILES: CC1NCc2nc(-c3ncccn3)ncc21]

A mixture of tert-butyl 5-methyl-2-pyrimidin-2-yl-5,7-dihydropyrrolo[3,4-d]pyrimidine-6-carboxylate (628.0 mg, 2.0 mmol) and a solution of HCl in EA (20 mL, 4M) was stirred at rt for 15 hrs under N₂. The resulting reaction mixture was concentrated in vacuo and the residue was diluted with MeOH (20 mL). The resulting solution was neutralized with basic resin and filtered. The filtrate was concentrated in vacuo to give crude 5-methyl-2-pyrimidin-2-yl-6,7-dihydro-5H-pyrrolo[3,4-d]pyrimidine (436.0 mg) as red solid, which was used in the next step without any further purification.

Step 2: Preparation of 6-(6-fluoro-4-methoxy-2-pyridyl)-5-methyl-2-pyrimidin-2-yl-5,7-dihydropyrrolo[3,4-d]pyrimidine

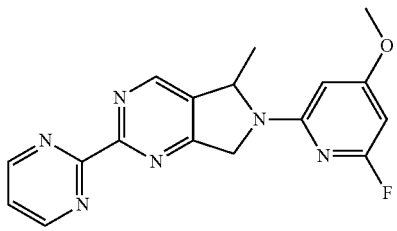 [SMILES: COc1cc(F)nc(N2Cc3nc(-c4ncccn4)ncc3C2C)c1]

A mixture of 5-methyl-2-pyrimidin-2-yl-6,7-dihydro-5H-pyrrolo[3,4-d]pyrimidine (400.0 mg, 1.8 mmol), 2,6-difluoro-4-methoxypyridine (406.0 mg, 2.8 mmol) and DIPEA (696.0 mg, 5.4 mmol) in NMP (12 mL) was heated at 120° C. with stirring for 5 hrs. The resulting reaction mixture was poured into saturated aqueous NaHCO₃ (20 mL) and extracted with DCM (20 mL) for three times. The combined organic phase was washed with brine, dried over anhydrous Na₂SO₄ and concentrated in vacuo. The residue was purified by prep-HPLC to give 6-(6-fluoro-4-methoxy-2-pyridyl)-5-methyl-2-pyrimidin-2-yl-5,7-dihydropyrrolo[3,4-d]pyrimidine (62.3 mg) as white solid. ¹H NMR (400 MHz, CDCl₃) δ ppm: 9.06 (s, 2H), 8.91 (s, 1H), 7.48-7.46 (t, 1H), 5.88 (s, 1H), 5.81 (s, 1H), 5.58-5.56 (m, 1H), 4.93-4.80 (m, 2H), 3.88 (s, 3H), 1.70-1.68 (d, 3H). MS obsd. (ESI⁺) [(M+H)⁺]: 339.

Example 31 and 32

6-(4,6-Difluoro-2-Pyridyl)-5-Methyl-2-Pyrimidin-2-Yl-5,7-Dihydropyrrolo[3,4-d]Pyrimidine and 6-(2,6-Difluoro-4-Pyridyl)-5-Methyl-2-Pyrimidin-2-Yl-5,7-Dihydropyrrolo[3,4-d]Pyrimidine

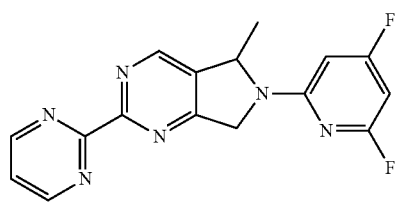

Example 31

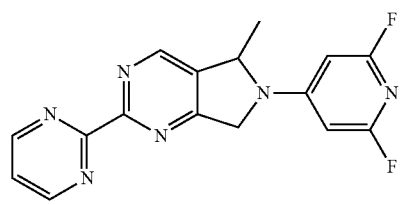

Example32

A mixture of 2,4,6-trifluoropyridine (1.9 g, 14.07 mmol), 5-methyl-2-pyrimidin-2-yl-6,7-dihydro-5H-pyrrolo[3,4-d]pyrimidine (1.5 g, 7.03 mmol) and DIPEA (3.68 mL, 21.1 mmol) in NMP (15 mL) was heated at 150° C. with stirring in a microwave reactor for 1 hr. The resulting reaction mixture was diluted with H₂O (100 mL) and extracted with EA (100 mL) for three times. The combined organic layer was dried over anhydrous MgSO₄ and concentrated in vacuo. The residue was purified by prep-HPLC to give 6-(4,6-difluoro-2-pyridyl)-5-methyl-2-pyrimidin-2-yl-5,7-dihydropyrrolo[3,4-d]pyrimidine (400 mg) as light yellow solid and 6-(2,6-difluoro-4-pyridyl)-5-methyl-2-pyrimidin-2-yl-5,7-dihydropyrrolo[3,4-d]pyrimidine (640 mg) as light yellow solid.

Example 31

6-(4,6-difluoro-2-pyridyl)-5-methyl-2-pyrimidin-2-yl-5,7-dihydropyrrolo[3,4-d]pyrimidine, ¹H NMR (400 MHz, CDCl₃) δ ppm: 9.06 (d, 2H), 8.93 (s, 1H), 7.48 (t, 1H), 7.28 (s, 1H), 6.05 (d, 2H), 5.57 (dd, 1H), 5.31 (s, 1H), 4.80-4.94 (m, 2H), 1.70 (d, 3H). MS obsd. (ESI+) [(M+H)⁺]: 327.

Example 32

6-(2,6-difluoro-4-pyridyl)-5-methyl-2-pyrimidin-2-yl-5,7-dihydropyrrolo[3,4-d]pyrimidine, ¹H NMR (400 MHz, CDCl₃) δ ppm: 9.07 (d, 2H), 8.97 (s, 1H), 7.50 (t, 1H), 7.28 (s, 1H), 6.08 (s, 2H), 5.35 (dd, 1H), 4.93 (dd, 1H), 4.80 (d, 1H), 1.67 (d, 3H). MS obsd. (ESI⁺) [(M+H)⁺]: 327.

Example 33

6-(6-Fluoro-4-methoxy-2-pyridyl)-5-methyl-2-(2-pyridyl)-5,7-dihydropyrrolo[3,4-d]pyrimidine

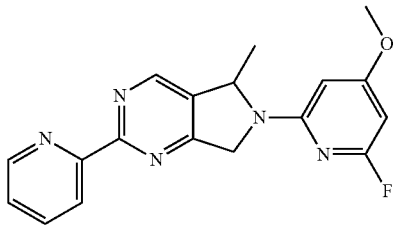 [SMILES: COc1cc(F)nc(N2Cc3nc(-c4ccccn4)ncc3C2C)c1]

Step 1: Preparation of tert-butyl 5-methyl-2-(2-pyridyl)-5,7-dihydropyrrolo[3,4-d]pyrimidine-6-carboxylate

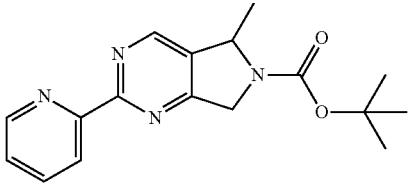 [SMILES: CC1c2cnc(-c3ccccn3)nc2CN1C(=O)OC(C)(C)C]

A mixture of tert-butyl 2-methyl-4-oxo-pyrrolidine-1-carboxylate (3.0 g, 15.0 mmol) and DMFDMA (30 mL) was heated at 120° C. with stirring for 12 hrs under N₂. The resulting reaction mixture was concentrated in vacuo and the residue was dissolved in EtOH (40 mL). To the solution was added pyridine-2-carboximidamide hydrochloride (2.4 g, 15.0 mmol) and K₂CO₃ (6.2 g, 45.0 mmol). The mixture was heated at 60° C. with stirring for 2 hrs under N₂. The resulting reaction mixture was concentrated in vacuo and the residue was purified prep-HPLC to give tert-butyl 5-methyl-2-(2-pyridyl)-5,7-dihydropyrrolo[3,4-d]pyrimidine-6-carboxylate (1.2 g) as red oil.

Step 2: Preparation of 5-methyl-2-(2-pyridyl)-6,7-dihydro-5H-pyrrolo[3,4-d]pyrimidine

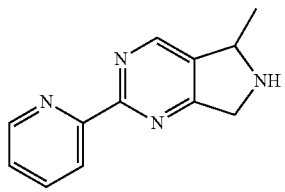 [SMILES: CC1NCc2nc(-c3ccccn3)ncc21]

A mixture of tert-butyl 5-methyl-2-(2-pyridyl)-5,7-dihydropyrrolo[3,4-d]pyrimidine-6-carboxylate (800 mg, 2.6 mmol) and a solution of HCl in EA (10 mL, 2M) was stirred at rt for 15 hrs under N₂. The resulting reaction mixture was concentrated in vacuo and the residue was dissolved in MeOH (10 mL). The resulting mixture was stirred with basic resin for 4 hrs at rt and then filtered. The filtrate was concentrated in vacuo to give 5-methyl-2-(2-pyridyl)-6,7- dihydro-5H-pyrrolo[3,4-d]pyrimidine (400 mg, crude) as brown oil, which was used in the next step without any further purification.

Step 3: Preparation of 6-(6-fluoro-4-methoxy-2-pyridyl)-5-methyl-2-(2-pyridyl)-5,7-dihydropyrrolo[3,4-d]pyrimidine

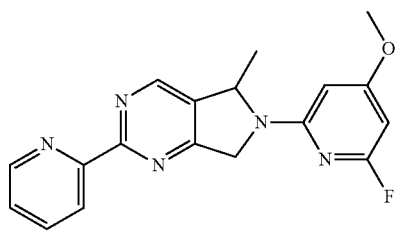

A mixture of 5-methyl-2-(2-pyridyl)-6,7-dihydro-5H-pyrrolo[3,4-d]pyrimidine (200 mg, 0.8 mmol), 2,6-difluoro-4-methoxypyridine (175 mg, 1.2 mmol) and DIPEA (310 mg, 2.4 mmol) in NMP (5 mL) was heated at 120° C. with stirring for 15 hrs. The resulting mixture was poured into aqueous saturated NaHCO₃ (20 mL) and extracted with DCM (30 mL) for three times. The combined organic phases were washed with brine (20 mL), dried over anhydrous Na₂SO₄ and concentrated in vacuo. The residue was purified by prep-HPLC to give 6-(6-fluoro-4-methoxy-2-pyridyl)-5-methyl-2-(2-pyridyl)-5,7-dihydropyrrolo[3,4-d]pyrimidine (5 mg) as light yellow solid. ¹H NMR (400 MHz, CDCl₃) δ ppm: 9.00-9.14 (m, 1H), 8.89 (s, 1H), 8.82 (d, 1H), 8.32 (br t, 1H), 7.82 (br t, 1H), 5.84-5.92 (m, 2H), 5.52-5.59 (m, 1H), 4.78-4.92 (m, 2H), 3.90 (s, 3H), 3.14 (br d, 1H), 1.70 (d, 3H). MS obsd. (ESI⁺) [(M+H)⁺]: 338.

Example 34

1-[4-[4-Fluoro-6-(5-Methyl-2-Pyrimidin-2-Yl-5,7-Dihydropyrrolo[3,4-d]Pyrimidin-6-Yl)-2-Pyridyl]Piperazin-1-Yl]Ethanone

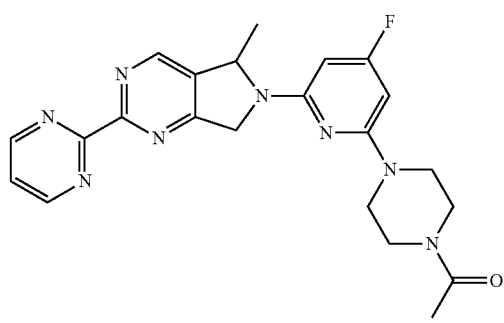 [SMILES: CC(=O)N1CCN(c2cc(F)cc(N3Cc4nc(-c5ncccn5)ncc4C3C)n2)CC1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), 1-(piperazin-1-yl)ethanone (76.9 mg, 0.6 mmol) and DIPEA (77.5 mg, 0.6 mmol) in DMSO (2 mL) was heated at 120° C. with stirring for 20 hrs. The resulting reaction mixture was diluted with H₂O (20 mL) and extracted with DCM (20 mL) for three times. The combined organic layer was washed with brine, dried over anhydrous Na₂SO₄ and concentrated in vacuo. The crude was purified by prep-HPLC to afford 1-[4-[4-fluoro-6-(5-methyl-2-pyrimidin-2-yl-5,7-dihydropyrrolo[3,4-d]pyrimidin-6-yl)-2-pyridyl]-piperazin-1-yl]ethanone (5 mg) as a yellow powder. ¹H NMR (400 MHz, DMSO-d₆) δ ppm: 9.13-8.97 (m, 3H), 7.66 (t, 1H), 6.03 (dd, 1H), 5.93-5.81 (dd, 1H), 5.50 (br d, 1H), 4.89-4.66 (m, 2H), 3.64-3.48 (m, 8H), 2.05 (s, 3H), 1.62 (d, 3H). MS obsd. (ESI⁺) [(M+H)⁺]: 435.

Example 35

6-[6-Fluoro-4-(5-Methyl-2-Pyrimidin-2-Yl-5,7-Dihydropyrrolo[3,4-d]Pyrimidin-6-Yl)-2-Pyridyl]-2-Oxa-6-Azaspiro[3.3]Heptane

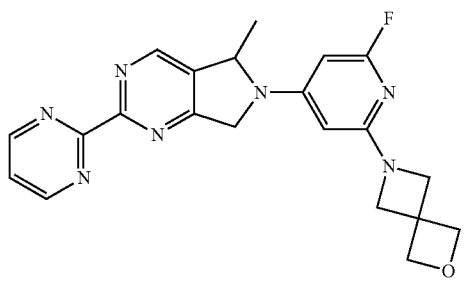 [SMILES: CC1c2cnc(-c3ncccn3)nc2CN1c1cc(F)nc(N2CC3(COC3)C2)c1]

A mixture of 6-(2,6-difluoro-4-pyridyl)-5-methyl-2-pyrimidin-2-yl-5,7-dihydropyrrolo[3,4-d]pyrimidine (Example 32, 131 mg, 0.4 mmol), 2-oxa-6-azaspiro[3.3]heptane hemioxalate (173 mg, 0.6 mmol) and DIPEA (77.5 mg, 0.6 mmol) in DMSO (2 mL) was heated at 130° C. with stirring for 20 hrs. The resulting reaction mixture was diluted with H₂O (20 mL) and extracted with DCM (30 mL) for three times. The combined organic layer was washed with brine, dried over anhydrous Na₂SO₄ and concentrated in vacuo. The residue was purified by prep-HPLC to afford 6-[6-fluoro-4-(5-methyl-2-pyrimidin-2-yl-5,7-dihydropyrrolo[3,4-d]pyrimidin-6-yl)-2-pyridyl]-2-oxa-6-azaspiro[3.3]heptane (9 mg) as a yellow powder. ¹H NMR (400 MHz, DMSO-d₆) δ ppm: 9.10-8.97 (m, 3H), 7.67 (t, 1H), 5.80 (s, 1H), 5.51-5.35 (m, 2H), 4.89-4.65 (m, 6H), 4.15-4.04 (m, 4H), 1.52 (d, 3H). MS obsd. (ESI⁺) [(M+H)⁺]: 406.

Example 36

6-[4-Fluoro-6-(5-Methyl-2-Pyrimidin-2-Yl-5,7-Dihydropyrrolo[3,4-d]Pyrimidin-6-Yl)-2-Pyridyl]-2-Oxa-6-Azaspiro[3.3]Heptane

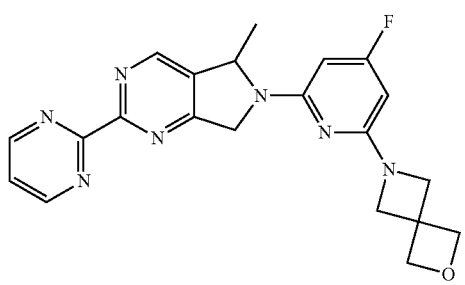 [SMILES: CC1c2cnc(-c3ncccn3)nc2CN1c1cc(F)cc(N2CC3(COC3)C2)n1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), 2-oxa-6-azaspiro[3.3]heptane hemioxalate (173 mg, 0.6 mmol) and DIPEA (77.5 mg, 0.6 mmol) in DMSO (2 mL) was heated at 130° C. with stirring for 20 hrs. The resulting reaction mixture was diluted with H$_2$O (20 mL) and extracted with DCM (30 mL) for three times. The combined organic layer was washed with brine, dried over anhydrous Na$_2$SO$_4$ and concentrated in vacuo. The crude was purified by prep-HPLC to afford 6-[4-fluoro-6-(5-methyl-2-pyrimidin-2-yl-5,7-dihydropyrrolo[3,4-d]pyrimidin-6-yl)-2-pyridyl]-2-oxa-6-azaspiro[3.3] heptane (3 mg) as a yellow powder. $^1$H NMR (400 MHz, DMSO-d$_6$) δ ppm: 9.10-8.95 (m, 3H), 7.66 (t, 1H), 5.49-5.36 (m, 3H), 4.85-4.64 (m, 6H), 4.12 (m, 4H), 1.57 (d, 3H). MS obsd. (ESI$^+$) [(M+H)$^+$]: 406.

Example 37

2-Fluoro-N-methyl-6-(5-methyl-2-pyrimidin-2-yl-5,7-dihydropyrrolo[3,4-d]pyrimidin-6-yl)pyridin-4-amine

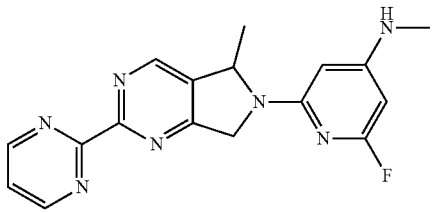 [SMILES: CNc1cc(F)nc(N2Cc3nc(-c4ncccn4)ncc3C2C)c1]

A mixture of 6-(4,6-difluoro-2-pyridyl)-5-methyl-2-pyrimidin-2-yl-5,7-dihydropyrrolo[3,4-d]pyrimidine (Example 31, 97.9 mg, 0.3 mmol), methanamine hydrochloride (101 mg, 1.5 mmol) and DIPEA (233 mg, 1.8 mmol) in DMSO (1 mL) was heated at 110° C. for 1 hr in a microwave reactor. After being cooled to rt, the resulting reaction mixture was purified by prep-HPLC to afford 2-fluoro-N-methyl-6-(5-methyl-2-pyrimidin-2-yl-5,7-dihydropyrrolo[3,4-d]pyrimidin-6-yl)pyridin-4-amine (48 mg) as a light yellow powder. $^1$H NMR (400 MHz, DMSO-d6) δ ppm: 9.04-8.98 (m, 3H), 7.66 (t, 1H), 6.66 (br d, 1H), 5.56 (s, 1H), 5.44-5.34 (m, 1H), 4.83-4.65 (m, 2H), 3.76-3.66 (m, 1H), 2.75 (d, 3H), 1.58 (d, 3H). MS obsd. (ESI$^+$) [(M+H)$^+$]: 338.

Example 38

2-Fluoro-N,N-dimethyl-6-(5-methyl-2-pyrimidin-2-yl-5,7-dihydropyrrolo[3,4-d]pyrimidin-6-yl)pyridin-4-amine

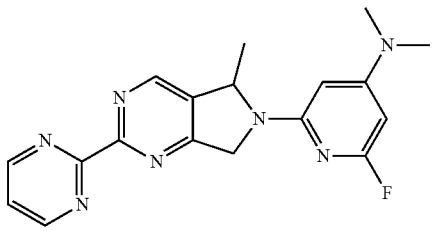 [SMILES: CC1c2cnc(-c3ncccn3)nc2CN1c1cc(N(C)C)cc(F)n1]

A mixture of 6-(4,6-difluoro-2-pyridyl)-5-methyl-2-pyrimidin-2-yl-5,7-dihydropyrrolo[3,4-d]pyrimidine (Example 31, 97.9 mg, 0.3 mmol), dimethylamine hydrochloride (122 mg, 1.5 mmol) and DIPEA (233 mg, 1.8 mmol) in DMSO (1 mL) was heated at 110° C. for 1 hr in a microwave reactor. After being cooled to rt, the resulting reaction mixture was purified by prep-HPLC to afford 2-fluoro-N,N-dimethyl-6-(5-methyl-2-pyrimidin-2-yl-5,7-dihydropyrrolo[3,4-d]pyrimidin-6-yl)pyridin-4-amine (45 mg) as a light yellow powder. $^1$H NMR (400 MHz, DMSO-d6) δ ppm: 9.10-8.95 (m, 3H), 7.66 (t, 1H), 5.72 (s, 1H), 5.59 (s, 1H), 5.50-5.40 (m, 1H), 4.87-4.69 (m, 2H), 3.00 (s, 6H), 1.59 (d, 3H). MS obsd. (ESI$^+$) [(M+H)$^+$]: 352.

Example 39

6-[4-(Azetidin-1-yl)-6-fluoro-2-pyridyl]-5-methyl-2-pyrimidin-2-yl-5,7-dihydropyrrolo[3,4-d]pyrimidine

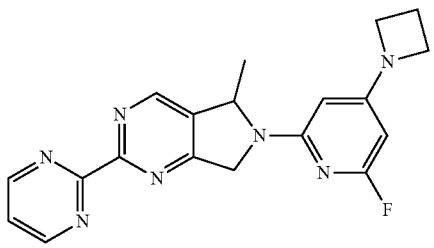 [SMILES: CC1c2cnc(-c3ncccn3)nc2CN1c1cc(N2CCC2)cc(F)n1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), azetidine hydrochloride (56.1 mg, 0.6 mmol) and DIPEA (233 mg, 0.8 mmol) in DMSO (1 mL) was heated at 110° C. for 1 hr in a microwave reactor. After being cooled to rt, the resulting reaction mixture was purified by prep-HPLC to afford 6-[4-(azetidin-1-yl)-6-fluoro-2-pyridyl]-5-methyl-2-pyrimidin-2-yl-5,7-dihydropyrrolo[3,4-d]pyrimidine (22 mg) as a light yellow powder. $^1$H NMR (400 MHz, DMSO-d6) δ ppm: 9.05-8.98 (m, 3H), 7.66 (t, 1H), 5.46-5.33 (m, 3H), 4.84-4.67 (m, 2H), 3.94 (t, 4H), 2.35 (quin, 2H), 1.58 (d, 3H). MS obsd. (ESI$^+$) [(M+H)$^+$]: 364.

Example 40

6-(6-Fluoro-4-pyrrolidin-1-yl-2-pyridyl)-5-methyl-2-pyrimidin-2-yl-5,7-dihydropyrrolo[3,4-d]pyrimidine

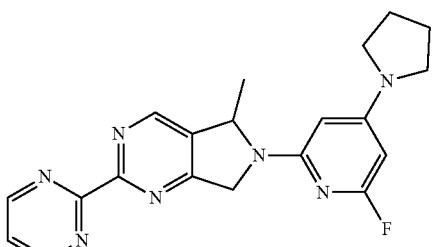

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), pyrrolidine (42.7 mg, 0.6 mmol) and DIPEA (233 mg, 0.8 mmol) in DMSO (1 mL) was heated at 110° C. for 1 hr in a microwave reactor. After being cooled to rt, the resulting reaction mixture was purified by prep-HPLC to afford 6-(6-fluoro-4-pyrrolidin-1-yl-2-pyridyl)-5-methyl-2-pyrimidin-2-yl-5,7-dihydropyrrolo[3,4-d]pyrimidine (21 mg) as a light yellow powder. $^1$H NMR (400 MHz, DMSO-d6) δ ppm: 8.99-8.90 (m, 3H), 7.59 (t, 1H), 5.50 (s, 1H), 5.44-5.33 (m, 2H), 4.79-4.62 (m, 2H), 3.25-3.21 (m, 4H), 1.96-1.84 (m, 4H), 1.52 (d, 3H). MS obsd. (ESI$^+$) [(M+H)$^+$]: 378.

Example 41

6-[6-Fluoro-4-(1-piperidyl)-2-pyridyl]-5-methyl-2-pyrimidin-2-yl-5,7-dihydropyrrolo[3,4-d]pyrimidine

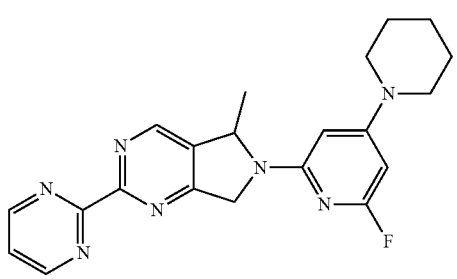 [SMILES: CC1c2cnc(-c3ncccn3)nc2CN1c1cc(N2CCCCC2)cc(F)n1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), piperidine (51.1 mg, 0.6 mmol) and DIPEA (233 mg, 0.8 mmol) in DMSO (1 mL) was heated at 110° C. for 1 hr in a microwave reactor. After being cooled to rt, the resulting reaction mixture was purified by prep-HPLC to afford 6-[6-fluoro-4-(1-piperidyl)-2-pyridyl]-5-methyl-2-pyrimidin-2-yl-5,7-dihydropyrrolo[3,4-d]pyrimidine (35 mg) as a light yellow powder. $^1$H NMR (400 MHz, DMSO-d6) δ ppm: 8.99-8.90 (m, 3H), 7.59 (t, 1H), 5.83 (s, 1H), 5.73 (s, 1H), 5.43-5.34 (m, 1H), 4.79-4.61 (m, 2H), 3.35-3.29 (m, 4H), 1.60-1.45 (m, 9H). MS obsd. (ESI$^+$) [(M+H)$^+$]: 392.

Example 42

4-[2-Fluoro-6-(5-methyl-2-pyrimidin-2-yl-5,7-dihydropyrrolo[3,4-d]pyrimidin-6-yl)-4-pyridyl]morpholine

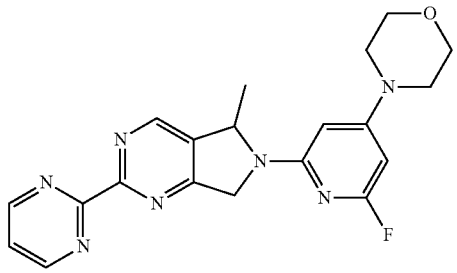 [SMILES: CC1c2cnc(-c3ncccn3)nc2CN1c1cc(N2CCOCC2)cc(F)n1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), morpholine (52.3 mg, 0.6 mmol) and DIPEA (233 mg, 0.8 mmol) in DMSO (1 mL) was heated at 110° C. for 1 hr in a microwave reactor. After being cooled to rt, the resulting reaction mixture was purified by prep-HPLC to afford 4-[2-fluoro-6-(5-methyl-2-pyrimidin-2-yl-5,7-dihydropyrrolo[3,4-d]pyrimidin-6-yl)-4-pyridyl]morpholine (28 mg) as a light yellow powder. $^1$H NMR (400 MHz, DMSO-d6) δ ppm: 8.99-8.92 (m, 3H), 7.59 (t, 1H), 5.89 (s, 1H), 5.79 (s, 1H), 5.44-5.34 (m, 1H), 4.81-4.64 (m, 2H), 3.68-3.61 (m, 4H), 3.26-3.23 (m, 4H), 1.51 (d, 3H). MS obsd. (ESI$^+$) [(M+H)$^+$]: 394.

Example 43

6-(6-Fluoro-4-piperazin-1-yl-2-pyridyl)-5-methyl-2-pyrimidin-2-yl-5,7-dihydropyrrolo[3,4-d]pyrimidine

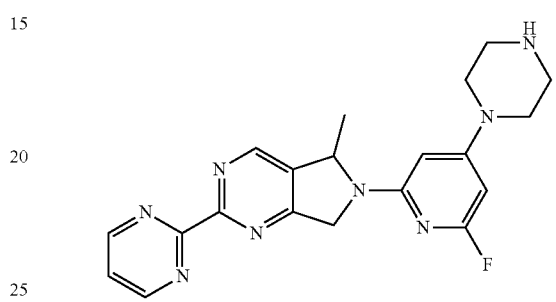

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), piperazine (51.7 mg, 0.6 mmol,) and DIPEA (233 mg, 0.8 mmol) in DMSO (1 mL) was heated at 110° C. for 1 hr in a microwave reactor. After being cooled to rt, the resulting reaction mixture was purified by prep-HPLC to afford 6-(6-fluoro-4-piperazin-1-yl-2-pyridyl)-5-methyl-2-pyrimidin-2-yl-5,7-dihydropyrrolo[3,4-d]pyrimidine (43 mg) as a light yellow powder. $^1$H NMR (400 MHz, DMSO-d6) δ ppm: 8.98-8.92 (m, 3H), 7.59 (t, 1H), 5.84 (s, 1H), 5.74 (s, 1H), 5.43-5.34 (m, 1H), 4.80-4.61 (m, 2H), 3.21-3.17 (m, 4H), 2.77-2.68 (m, 4H), 1.51 (d, 3H). MS obsd. (ESI$^+$) [(M+H)$^+$]: 393.

Example 44

6-[6-Fluoro-4-(4-methylsulfonylpiperazin-1-yl)-2-pyridyl]-5-methyl-2-pyrimidin-2-yl-5,7-dihydropyrrolo[3,4-d]pyrimidine

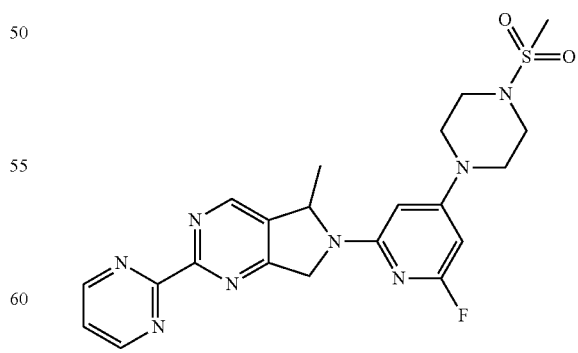

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), 1-(methylsulfonyl)piperazine (98.5 mg, 0.6 mmol) and DIPEA (233 mg, 0.8 mmol)

in DMSO (1 mL) was heated at 130° C. for 3 hrs in a microwave reactor. After being cooled to rt, the resulting reaction mixture was purified by prep-HPLC to afford 6-[6-fluoro-4-(4-methylsulfonylpiperazin-1-yl)-2-pyridyl]-5-methyl-2-pyrimidin-2-yl-5,7-dihydropyrrolo[3,4-d]pyrimidine (23 mg) as a light yellow powder. $^1$H NMR (400 MHz, DMSO-d6) δ ppm: 8.98-8.90 (m, 3H), 7.59 (t, 1H), 5.93 (s, 1H), 5.83 (s, 1H), 5.45-5.34 (m, 1H), 4.82-4.63 (m, 2H), 3.51-3.40 (m, 4H), 3.19-3.09 (m, 4H), 2.86 (s, 3H), 1.51 (d, 3H). MS obsd. (ESI$^+$) [(M+H)$^+$]: 471.

Example 45

4-[2-Fluoro-6-(5-methyl-2-pyrimidin-2-yl-5,7-dihydropyrrolo[3,4-d]pyrimidin-6-yl)-4-pyridyl]piperazin-2-one

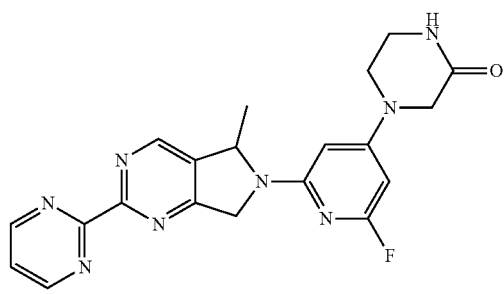 [SMILES: CC1c2cnc(-c3ncccn3)nc2CN1c1cc(N2CCNC(=O)C2)cc(F)n1]

A mixture of 6-(4,6-difluoro-2-pyridyl)-5-methyl-2-pyrimidin-2-yl-5,7-dihydropyrrolo[3,4-d]pyrimidine (Example 31, 65.3 mg, 0.2 mmol), piperazin-2-one (60.1 mg, 0.6 mmol,) and DIPEA (233 mg, 0.8 mmol) in DMSO (1 mL) was heated at 130° C. for 3 hrs in a microwave reactor. After being cooled to rt, the resulting reaction mixture was purified by prep-HPLC to afford 4-[2-fluoro-6-(5-methyl-2-pyrimidin-2-yl-5,7-dihydropyrrolo[3,4-d]pyrimidin-6-yl)-4-pyridyl]piperazin-2-one (13 mg) as a light yellow powder. $^1$H NMR (400 MHz, DMSO-d6) δ ppm: 9.05-8.97 (m, 3H), 8.20 (br s, 1H), 7.66 (t, 1H), 5.93 (s, 1H), 5.80 (s, 1H), 5.48 (br d, 1H), 4.89-4.72 (m, 2H), 3.93 (s, 2H), 3.56 (br t, 2H), 3.35-3.27 (m, 2H), 1.59 (d, 3H). MS obsd. (ESI$^+$) [(M+H)$^+$]: 407.

Biological Examples

Example 46

Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 µL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration (or conditioned media log dilution) at which HBsAg secretion was reduced by 50% compared to the no drug control.

The compounds according to formula I were tested for their capacity to inhibit HBsAg as described herein. The Examples were tested in the above assay and found to have IC$_{50}$ below 50 µM. Particular compounds of formula I were found to have IC$_{50}$ below 0.50 µM. More Particular compounds of formula I were found to have IC$_{50}$ below 0.100 µM. Results of HBsAg assay are given in Table 1.

TABLE 1

Activity data in HBsAg assay

| Example No. | IC$_{50}$ (µM) | Example No. | IC$_{50}$ (µM) | Example No. | IC$_{50}$ (µM) | Example No. | IC$_{50}$ (µM) |
|---|---|---|---|---|---|---|---|
| 1 | 0.7 | 13 | 3.537 | 25 | 28.982 | 37 | 0.055 |
| 2 | 0.33 | 14 | 0.422 | 26 | 0.22 | 38 | 0.015 |
| 3 | 0.546 | 15 | 26.098 | 27 | 0.62 | 39 | 0.02 |
| 4 | 14.06 | 16 | 4.692 | 28 | 1.79 | 40 | 0.016 |
| 5 | 1.7 | 17 | 0.761 | 29 | 3.43 | 41 | 0.041 |
| 6 | 1.111 | 18 | 0.724 | 30 | 0.05 | 42 | 0.04 |
| 7 | 0.92 | 19 | 7.862 | 31 | 0.659 | 43 | 4.27 |
| 8 | 0.681 | 20 | 0.502 | 32 | 2.003 | 44 | 0.14 |
| 9 | 0.38 | 21 | 0.219 | 33 | 0.127 | 45 | 0.16 |
| 10 | 0.282 | 22 | 4.733 | 34 | 0.361 | | |
| 11 | 6.167 | 23 | 0.232 | 35 | 0.588 | | |
| 12 | 0.158 | 24 | 0.156 | 36 | 0.865 | | |

HBV DNA Assay

The assay employs real-time qPCR (TaqMan) to directly measure extracellular HBV DNA copy number in the cell supernatant, HepG2.2.15 cells were plated in 96-well microtiter plates before treatment with complete medium (DMEM, Glutamax, 10% FBS, 1% Penicillin/Streptomycin, 250 µg/mL Genetycin, final DMSO concentration is 1%). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 µM, 2 µM or 0.5 µM according to the HBsAg IC50 observed, with ⅓ successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels ($IC_{50}$).

The compounds of the present invention were tested for their capacity to inhibit HBV DNA as described herein. The Examples were tested in the above assay and found to have $IC_{50}$ below 50 µM. Particular compounds of formula I were found to have $IC_{50}$ below 500 nM. More Particular compounds of formula I were found to have $IC_{50}$ below 100 nM. Results of HBV DNA assay are given in Table 2.

TABLE 2

Anti HBV DNA production activity in HepG2.2.15 cells

| Example No. | $IC_{50}$ (nM) |
|---|---|
| 10 | 67.6 |
| 12 | 5.6 |
| 21 | 26.2 |
| 30 | 6.5 |

The invention claimed is:

1. A compound of formula I,

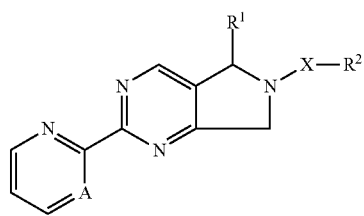

(I)

wherein:
R¹ is amino$C_{1-6}$alkyl, $C_{1-6}$alkyl, $C_{3-7}$cycloalkyl, carboxy$C_{1-6}$alkyl, cyano$C_{1-6}$alkyl, halo$C_{1-6}$alkyl, hydrogen or hydroxy$C_{1-6}$alkyl;
R² is phenyl, naphthyl, or heteroaryl, wherein said phenyl, naphthyl and heteroaryl are unsubstituted or substituted with one, two or three substituents independently selected from 2-oxa-6-azaspiro[3.3]heptanyl, azetidinyl, $C_{1-6}$alkoxy, $C_{1-6}$ alkyl, $C_{1-6}$alkylamino, $C_{1-6}$alkylcarbonylpiperazinyl, $C_{1-6}$alkylsulfonylpiperazinyl, di$C_{1-6}$alkylamino, halo$C_{1-6}$alkyl, halogen, morpholinyl, nitro, oxopiperazinyl, piperazinyl, piperidinyl and pyrrolidinyl;
A is N or CH; and
X is a bond or —C(=O)—;
or a pharmaceutically acceptable salt, or enantiomer, or diastereomer thereof.

2. A compound according to claim 1, wherein:
R¹ is $C_{1-6}$alkyl or hydrogen;
R² is phenyl, naphthyl or heteroaryl, wherein said phenyl and heteroaryl are unsubstituted or substituted with one, two or three substituents independently selected from 2-oxa-6-azaspiro[3.3]heptanyl, azetidinyl, $C_{1-6}$alkoxy, $C_{1-6}$alkyl, $C_{1-6}$alkylamino, $C_{1-6}$alkylcarbonylpiperazinyl, $C_{1-6}$alkylsulfonylpiperazinyl, di$C_{1-6}$alkylamino, halo$C_{1-6}$alkyl, halogen, morpholinyl, nitro, oxopiperazinyl, piperazinyl, piperidinyl and pyrrolidinyl;
A is N or CH; and
X is a bond or —C(=O)—;
or a pharmaceutically acceptable salt, or enantiomer, or diastereomer thereof.

3. A compound according to claim 1, wherein:
R¹ is $C_{1-6}$alkyl;
R² is phenyl, naphthyl or heteroaryl, wherein said phenyl and heteroaryl are unsubstituted or substituted with one, two or three substituents independently selected from $C_{1-6}$alkyl, $C_{1-6}$alkoxy, halo$C_{1-6}$alkyl, halogen and nitro; said heteroaryl is 1,2-benzoxazolyl, 1,3-benzothiazolyl, benzimidazolyl, indazolyl, benzofuranyl, imidazo[1,2-a]pyrazinyl, pyrazolo[1,5-a]pyridinyl, pyrazolyl, thiazolyl or thienyl;
A is N; and
X is —C(=O)—;
or a pharmaceutically acceptable salt, or enantiomer, or diastereomer thereof.

4. A compound according to claim 1, or a pharmaceutically acceptable salt, or enantiomer, or diastereomer thereof, wherein R¹ is methyl.

5. A compound according to claim 1, or a pharmaceutically acceptable salt, or enantiomer, or diastereomer thereof, wherein R¹ is indazolyl, $C_{1-6}$alkylindazolyl, $C_{1-6}$alkoxythienyl, $C_{1-6}$alkylthienyl or halothienyl.

6. A compound according to claim 1, or a pharmaceutically acceptable salt, or enantiomer, or diastereomer thereof, wherein R¹ is indazolyl, methylindazolyl, methoxythienyl, bromothienyl or chlorothienyl.

7. A compound according to claim 1, selected from:
(5-methyl-2-pyrimidin-2-yl-5,7-dihydropyrrolo[3,4-d]pyrimidin-6-yl)-(5-methylthiazol-2-yl)methanone;
(5-methoxy-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)[4-(trifluoromethyl)thiazol-2-yl]methanone;
(3-fluoro-5-methoxy-phenyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(2-thienyl)methanone;
(5-methyl-2-pyrimidin-2-yl-5,7-dihydropyrrolo[3,4-d]pyrimidin-6-yl)-(4-methyl-2-thienyl)methanone;
(4-bromo-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(5-methyl-2-thienyl)methanone;
(5-chloro-2-thienyl)-(5-methyl-2-pyrimidin-2-yl-5,7-dihydropyrrolo[3,4-d]pyrimidin-6-yl)methanone;
(4,5-dimethylthiazol-2-yl)-(5-methyl-2-pyrimidin-2-yl-5,7-dihydropyrrolo[3,4-d]pyrimidin-6-yl)methanone;
(1-methylpyrazol-4-yl)-(5-methyl-2-pyrimidin-2-yl-5,7-dihydropyrrolo[3,4-d]pyrimidin-6-yl)methanone;
(1-methylindazol-3-yl)-(5-methyl-2-pyrimidin-2-yl-5,7-dihydropyrrolo[3,4-d]pyrimidin-6-yl)methanone;
(1-methylpyrazol-3-yl)-(5-methyl-2-pyrimidin-2-yl-5,7-dihydropyrrolo[3,4-d]pyrimidin-6-yl)methanone;
1H-benzimidazol-2-yl-(5-methyl-2-pyrimidin-2-yl-5,7-dihydropyrrolo[3,4-d]pyrimidin-6-yl)methanone;
(4-methoxyphenyl)-(5-methyl-2-pyrimidin-2-yl-5,7-dihydropyrrolo[3,4-d]pyrimidin-6-yl)methanone;
(1-ethylpyrazol-3-yl)-(5-methyl-2-pyrimidin-2-yl-5,7-dihydropyrrolo[3,4-d]pyrimidin-6-yl)methanone;
(5-bromo-2-thienyl)-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-(5-nitro-2-thienyl)methanone;
(5-methyl-2-pyrimidin-2-yl-5,7-dihydropyrrolo[3,4-d]pyrimidin-6-yl)-(2-naphthyl)methanone;

imidazo[1,2-a]pyridin-2-yl-(5-methyl-2-pyrimidin-2-yl-5,7-dihydropyrrolo[3,4-d]pyrimidin-6-yl)methanone;
(3-methylbenzofuran-2-yl)-(5-methyl-2-pyrimidin-2-yl-5,7-dihydropyrrolo[3,4-d]pyrimidin-6-yl)methanone;
(6-methoxypyrazin-2-yl)-(5-methyl-2-pyrimidin-2-yl-5,7-dihydropyrrolo[3,4-d]pyrimidin-6-yl)methanone;
1H-indazol-3-yl-(5-methyl-2-pyrimidin-2-yl-5,7-dihydropyrrolo[3,4-d]pyrimidin-6-yl)methanone;
(5-methyl-2-pyrimidin-2-yl-5,7-dihydropyrrolo[3,4-d]pyrimidin-6-yl)-pyrazolo[1,5-a]pyridin-3-yl-methanone;
1,3-benzothiazol-6-yl-(5-methyl-2-pyrimidin-2-yl-5,7-dihydropyrrolo[3,4-d]pyrimidin-6-yl)methanone;
imidazo[1,2-a]pyridin-3-yl-(5-methyl-2-pyrimidin-2-yl-5,7-dihydropyrrolo[3,4-d]pyrimidin-6-yl)methanone;
1,2-benzoxazol-3-yl-(5-methyl-2-pyrimidin-2-yl-5,7-dihydropyrrolo[3,4-d]pyrimidin-6-yl)methanone; and
1,3-benzothiazol-2-yl-(5-methyl-2-pyrimidin-2-yl-5,7-dihydropyrrolo[3,4-d]pyrimidin-6-yl)methanone;
or a pharmaceutically acceptable salt, or enantiomer, or diastereomer thereof.

8. A compound according to claim 1, which is (1-methylindazol-3-yl)-(5-methyl-2-pyrimidin-2-yl-5,7-dihydropyrrolo[3,4-d]pyrimidin-6-yl)methanone; or a pharmaceutically acceptable salt, or enantiomer, or diastereomer thereof.

9. A compound according to claim 1, wherein:
$R^1$ is $C_{1-6}$alkyl or hydrogen;
$R^2$ is phenyl substituted with one, two or three substituents independently selected from halogen and $C_{1-6}$alkoxy; or pyridinyl substituted with one or two substituents independently selected from $C_{1-6}$alkoxy, 2-oxa-6-azaspiro[3.3]heptanyl, azetidinyl, $C_{1-6}$alkylamino, $C_{1-6}$alkylcarbonylpiperazinyl, $C_{1-6}$alkylsulfonylpiperazinyl, di$C_{1-6}$alkylamino, halogen, morpholinyl, oxopiperazinyl, piperazinyl, piperidinyl and pyrrolidinyl;
A is N or C; and
X is a bond;
or a pharmaceutically acceptable salt, or enantiomer, or diastereomer thereof.

10. A compound according to claim 1, or a pharmaceutically acceptable salt, or enantiomer, or diastereomer thereof, wherein $R^2$ is pyridinyl substituted with one or two substituents independently selected from $C_{1-6}$alkoxy, azetidinyl, $C_{1-6}$alkylamino, $C_{1-6}$alkylsulfonylpiperazinyl, di$C_{1-6}$alkylamino, halogen, and oxopiperazinyl.

11. A compound according to claim 1, or a pharmaceutically acceptable salt, or enantiomer, or diastereomer thereof, wherein $R^2$ is pyridinyl substituted with one or two substituents independently selected from methoxy, azetidinyl, methylamino, methylsulfonylpiperazinyl, dimethyl amino, fluoro and oxopiperazinyl.

12. A compound according to claim 1, or a pharmaceutically acceptable salt, or enantiomer, or diastereomer thereof, wherein A is N.

13. A compound according to claim 1, selected from:
6-(3,4-difluoro-5-methoxy-phenyl)-2-(2-pyridyl)-5,7-dihydropyrrolo[3,4-d]pyrimidine;
6-(6-fluoro-4-methoxy-2-pyridyl)-5-methyl-2-pyrimidin-2-yl-5,7-dihydropyrrolo[3,4-d]pyrimidine;
6-(4,6-difluoro-2-pyridyl)-5-methyl-2-pyrimidin-2-yl-5,7-dihydropyrrolo[3,4-d]pyrimidine;
6-(2,6-difluoro-4-pyridyl)-5-methyl-2-pyrimidin-2-yl-5,7-dihydropyrrolo[3,4-d]pyrimidine;
6-(6-fluoro-4-methoxy-2-pyridyl)-5-methyl-2-(2-pyridyl)-5,7-dihydropyrrolo[3,4-d]pyrimidine;
1-[4-[4-fluoro-6-(5-methyl-2-pyrimidin-2-yl-5,7-dihydropyrrolo[3,4-d]pyrimidin-6-yl)-2-pyridyl]piperazin-1-yl]ethanone;
6-[6-fluoro-4-(5-methyl-2-pyrimidin-2-yl-5,7-dihydropyrrolo[3,4-d]pyrimidin-6-yl)-2-pyridyl]-2-oxa-6-azaspiro[3.3]heptane;
6-[2-fluoro-6-(5-methyl-2-pyrimidin-2-yl-5,7-dihydropyrrolo[3,4-d]pyrimidin-6-yl)-4-pyridyl]-2-oxa-6-azaspiro[3.3]heptane;
2-fluoro-N-methyl-6-(5-methyl-2-pyrimidin-2-yl-5,7-dihydropyrrolo[3,4-d]pyrimidin-6-yl)pyridin-4-amine;
2-fluoro-N,N-dimethyl-6-(5-methyl-2-pyrimidin-2-yl-5,7-dihydropyrrolo[3,4-d]pyrimidin-6-yl)pyridin-4-amine;
6-[4-(azetidin-1-yl)-6-fluoro-2-pyridyl]-5-methyl-2-pyrimidin-2-yl-5,7-dihydropyrrolo[3,4-d]pyrimidine;
6-(6-fluoro-4-pyrrolidin-1-yl-2-pyridyl)-5-methyl-2-pyrimidin-2-yl-5,7-dihydropyrrolo[3,4-d]pyrimidine;
6-[6-fluoro-4-(1-piperidyl)-2-pyridyl]-5-methyl-2-pyrimidin-2-yl-5,7-dihydropyrrolo[3,4-d]pyrimidine;
4-[2-fluoro-6-(5-methyl-2-pyrimidin-2-yl-5,7-dihydropyrrolo[3,4-d]pyrimidin-6-yl)-4-pyridyl]morpholine;
6-(6-fluoro-4-piperazin-1-yl-2-pyridyl)-5-methyl-2-pyrimidin-2-yl-5,7-dihydropyrrolo[3,4-d]pyrimidine;
6-[6-fluoro-4-(4-methylsulfonylpiperazin-1-yl)-2-pyridyl]-5-methyl-2-pyrimidin-2-yl-5,7-dihydropyrrolo[3,4-d]pyrimidine; and
4-[2-fluoro-6-(5-methyl-2-pyrimidin-2-yl-5,7-dihydropyrrolo[3,4-d]pyrimidin-6-yl)-4-pyridyl]piperazin-2-one;
or a pharmaceutically acceptable salt, or enantiomer, or diastereomer thereof.

14. A compound according to claim 1, selected from:
6-(6-fluoro-4-methoxy-2-pyridyl)-5-methyl-2-pyrimidin-2-yl-5,7-dihydropyrrolo[3,4-d]pyrimidine;
2-fluoro-N-methyl-6-(5-methyl-2-pyrimidin-2-yl-5,7-dihydropyrrolo[3,4-d]pyrimidin-6-yl)pyridin-4-amine;
2-fluoro-N,N-dimethyl-6-(5-methyl-2-pyrimidin-2-yl-5,7-dihydropyrrolo[3,4-d]pyrimidin-6-yl)pyridin-4-amine;
6-[4-(azetidin-1-yl)-6-fluoro-2-pyridyl]-5-methyl-2-pyrimidin-2-yl-5,7-dihydropyrrolo[3,4-d]pyrimidine;
6-[6-fluoro-4-(4-methylsulfonylpiperazin-1-yl)-2-pyridyl]-5-methyl-2-pyrimidin-2-yl-5,7-dihydropyrrolo[3,4-d]pyrimidine; and
4-[2-fluoro-6-(5-methyl-2-pyrimidin-2-yl-5,7-dihydropyrrolo[3,4-d]pyrimidin-6-yl)-4-pyridyl]piperazin-2-one;
or a pharmaceutically acceptable salt, or enantiomer, or diastereomer thereof.

15. A pharmaceutical composition comprising a compound according to claim 1, or a pharmaceutically acceptable salt, or enantiomer, or diastereomer thereof, and a therapeutically inert carrier.

16. A method for the treatment or prophylaxis of HBV infection, which method comprises:
administering to a patient in need thereof an effective amount of a compound according to claim 1, or a pharmaceutically acceptable salt, or enantiomer, or diastereomer thereof.

17. A method for the inhibition of HBsAg production or secretion, or for the inhibition of HBV DNA production, which method comprises administering an effective amount of a compound according to claim 1, or a pharmaceutically acceptable salt, or enantiomer, or diastereomer thereof.

* * * * *